United States Patent
Samain et al.

(10) Patent No.: US 8,029,577 B2
(45) Date of Patent: *Oct. 4, 2011

(54) LIGHTENING AND/OR DYEING OF HUMAN KERATIN FIBRES VIA A COMPOSITION COMPRISING A PARTICULAR AMINO SILICON COMPOUND AND COMPOSITION AND DEVICE

(75) Inventors: Henri Samain, Bievres (FR); Leïla Hercouet, Neuilly Plaisance (FR)

(73) Assignee: L'Oreal S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 12/740,630

(22) PCT Filed: Oct. 31, 2008

(86) PCT No.: PCT/FR2008/051975
§ 371 (c)(1),
(2), (4) Date: Aug. 9, 2010

(87) PCT Pub. No.: WO2009/056778
PCT Pub. Date: May 7, 2009

(65) Prior Publication Data
US 2010/0297049 A1    Nov. 25, 2010

(30) Foreign Application Priority Data

Oct. 31, 2007   (FR) ..................... 07 58744

(51) Int. Cl.
*A61Q 5/10*    (2006.01)
*A61K 8/89*    (2006.01)

(52) U.S. Cl. ............. 8/405; 8/406; 8/410; 8/411; 8/431; 8/435; 8/501; 8/521; 8/581; 8/632; 132/202; 132/208; 424/70.12

(58) Field of Classification Search ............. 8/405, 406, 8/410, 411, 431, 435, 501, 521, 581, 632; 132/202, 208; 424/70.12
See application file for complete search history.

(56) References Cited

U.S. PATENT DOCUMENTS

| | | | |
|---|---|---|---|
| 4,344,763 A | 8/1982 | Tolgyesi et al. | |
| 2003/0150066 A1 | 8/2003 | Richard | |
| 2006/0110351 A1* | 5/2006 | Koehler et al. | ............ 424/70.12 |

FOREIGN PATENT DOCUMENTS

| | | |
|---|---|---|
| EP | 1 298 135 A1 | 4/2003 |
| FR | 2 891 143 A1 | 3/2007 |

OTHER PUBLICATIONS

STIC Search Report dated Sep. 30, 2010.*
International Search Report for PCT/FR2008/051975, dated Jun. 29, 2009.
English language abstract of FR 2 891 143 A1, Mar. 30, 2007.

* cited by examiner

*Primary Examiner* — Eisa Elhilo
(74) *Attorney, Agent, or Firm* — Finnegan, Henderson, Farabow, Garrett & Dunner L.L.P.

(57) ABSTRACT

The present disclosure provides a method of lightening and/or colouring human keratin fibers using at least one first composition comprising at least one specific aminosilicon compound and at least one oxidizing composition. It also provides a composition containing less than 10% by weight of water comprising at least one specific aminosilicon compound and at least one fatty substance. It provides, lastly, a multiple-compartment device in which at least one compartment comprises the abovementioned composition, and at least one other compartment comprises an oxidizing composition.

23 Claims, No Drawings

LIGHTENING AND/OR DYEING OF HUMAN KERATIN FIBRES VIA A COMPOSITION COMPRISING A PARTICULAR AMINO SILICON COMPOUND AND COMPOSITION AND DEVICE

This application is a national stage entry of International Application No. PCT/FR2008/051975, filed on Oct. 31, 2008, which claims priority to French Application No. FR 0758744, filed Oct. 31, 2007.

The present invention provides a method of lightening and/or colouring human keratin fibres using, on the one hand, a composition comprising a specific aminosilicon compound and, on the other hand, an oxidizing composition.

It also provides a specific composition comprising a specific aminosilicon compound and at least one fat.

It provides, lastly, a multiple-compartment device in which at least one compartment comprises the abovementioned composition and at least one other compartment comprises an oxidizing composition.

The techniques for colouring human keratin fibres such as the hair include permanent or oxidation colouring. This means of colouring, more particularly, employs one or more oxidation dye precursors, more particularly one or more oxidation bases optionally in combination with one or more couplers.

Oxidation bases are typically selected from ortho- or para-phenylenediamines, ortho- or para-aminophenols, and heterocyclic compounds. These oxidation bases are colourless or weakly coloured compounds which, in combination with oxidizing products, provide access to coloured species by a process of oxidative condensation.

The shades obtained with these oxidation bases are very often varied by combining them with one or more couplers, the latter being selected in particular from aromatic meta-diamines, meta-aminophenols, meta-diphenols, and certain heterocyclic compounds, such as indole compounds.

The variety of molecules employed as oxidation bases and couplers allows a rich palette of colours to be obtained.

The colouring method involves contacting the oxidation dye precursor or precursors with an oxidizing agent, which is preferably hydrogen peroxide, under alkaline conditions. One of the difficulties lies in the fact that the most commonly used alkaline agent is aqueous ammonia, whose function is to adjust the pH of the composition to an alkaline pH in order to allow the breakdown of the oxidizing agent. Hence the oxygen formed causes condensation of the oxidation dye precursors and a lightening of the fibre by virtue of the breakdown of the melanin present. The alkalifying agent also has another role, namely that of swelling the keratin fibre in order to promote the penetration of the oxidizing agent and the dyes to the interior of the fibre.

This alkalifying agent is highly volatile, and this causes unpleasantness to the user on account of the strong and fairly unpleasant odour of the ammonia which is given off during the procedure.

Moreover, the amount of ammonia given off requires the use of levels which are greater than those necessary, in order to compensate this loss. This is not without consequence for the user, who not only remains discomforted by the odour but may also be confronted with greater risks of intolerance, such as, for example, irritation of the scalp (stinging sensations).

The option purely and simply of replacing all or some of the aqueous ammonia by one or more other conventional alkalifying agents does not result in compositions which are as effective as those based on aqueous ammonia, particularly for the reason that these alkalifying agents do not provide sufficient lightening of the pigmented fibres in the presence of the oxidizing agent.

Another colouring technique employed is that of direct or semi-permanent colouring. This procedure involves applying direct dyes to the keratin fibres, said dyes being coloured and colouring molecules which have an affinity for the fibres, and then leaving them to take, to allow the molecules to penetrate by diffusion to the interior of the fibre, and then rinsing the fibres.

The direct dyes generally employed are selected from nitrobenzene, anthraquinonoid, nitropyridine, azo, methine, azomethine, xanthene, acridine, azine or triarylmethane direct dyes.

This colouring technique does not require the use of an oxidizing agent unless the desire is to lighten the fibre at the same time as colouring it. In the latter case, the procedure is as for oxidation dyeing, in other words contacting the keratin fibres with the dyeing composition in the presence of an oxidizing agent, more particularly hydrogen peroxide, under alkaline conditions, generally in the presence of aqueous ammonia. The user, consequently, is then confronted once again with the same difficulties as those set out before for oxidation dyeing.

Further to the colouring procedures, it is likewise common to employ lightening procedures in which the keratin fibres are contacted with an oxidizing composition under alkaline conditions. These procedures only involve breaking down the melanin in the hair, to a greater or lesser extent depending on the oxidizing agent selected. Thus a peroxygenated salt leads, generally speaking, to more pronounced lightening than when using hydrogen peroxide alone under alkaline conditions. Irrespective of the oxidizing agent employed, however, the lightening procedures require the use of hydrogen peroxide under alkaline conditions, and more particularly in the presence of aqueous ammonia, to form or accelerate the formation of oxygen. Consequently, once again, the same difficulties are encountered as those with the colouring procedures employed in the presence of an oxidizing agent and aqueous ammonia.

One of the objectives of the present invention is therefore to provide colouring and/or lightening compositions for human keratin fibres that are intended for use in the presence of an oxidizing agent but which do not exhibit the same disadvantages as the existing compositions, owing to the presence of large amounts of aqueous ammonia, while remaining at least equally effective, from the standpoints both of lightening and of colouring, and which display, more particularly, high performance in terms of chromaticity, power and homogeneity.

It should be noted that it was far from being obvious to employ amino silicon compounds corresponding to those of the formula (I) as alkalifying agents in this type of method.

The reason is that, in the presence of sufficient amounts of water, the majority of these amino silicon compounds rapidly undergo hydrolysis and condensation. The expectation would therefore have been a drop in the effectiveness of colouring and/or lightening, as a result of poor penetration of the silicon-based polymers resulting from this reaction into the fibre on account of their size, diminishing accordingly the lightening power or colouring power of the composition.

These aims and others are achieved by the present invention, which accordingly provides a method of colouring and/or lightening human keratin fibres, in which said fibres are contacted with:
  a first composition having a water content of less than 10% by weight and comprising one or more aminosilicon compounds of formula (I) below:

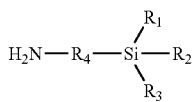

in which:

$R_1$, $R_2$ and $R_3$, which are identical or different, denote:
- a linear or branched $C_1$-$C_{20}$ alkoxy radical in which the alkyl moiety is optionally interrupted by one or more oxygen atoms, and more particularly a linear or branched $C_1$-$C_{20}$, preferably $C_1$-$C_4$, alkoxy radical,
- a linear or branched $C_2$-$C_{20}$, preferably $C_2$-$C_4$, alkenyloxy radical, $R_4$ is a divalent radical of structure:

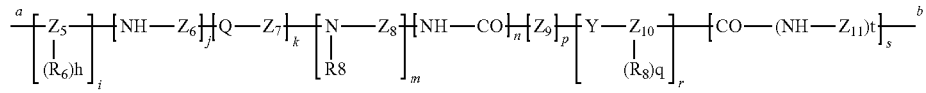

in which:
- $R_6$, identical or different at each occurrence, denotes a linear or branched $C_1$-$C_4$ alkyl radical, preferably methyl or ethyl, which is optionally substituted by one or more hydroxyl groups, an $NH_2$ radical, a hydroxyl radical, a cyano radical, a radical $Z_{12}NH_2$, a radical $Z_{13}NH Z_{14}NH_2$, a linear or branched $C_2$-$C_{10}$, preferably $C_2$-$C_4$, alkenyl radical, with $Z_{12}$, $Z_{13}$ and $Z_{14}$ denoting, independently of one another, a $C_1$-$C_{20}$, preferably $C_1$-$C_{10}$, more preferably $C_1$-$C_4$ linear alkylene radical
- $R_8$ denotes a linear or branched $C_1$-$C_4$ alkyl radical, preferably methyl or ethyl, which is optionally substituted by one or more hydroxyl or carboxyl groups, a linear or branched $C_2$-$C_{10}$, preferably $C_2$-$C_4$, alkenyl radical, a radical $Z_{15}NH_2$, a radical $Z_{16}R_8'$ or a radical $Z_{17}Si\,OSi(R_a)_2(R_b)$ where
  - $R_a$ denotes a linear or branched $C_1$-$C_4$ alkoxy radical, preferably methoxy or ethoxy
  - $R_b$ denotes a linear or branched $C_1$-$C_4$ alkyl radical, preferably methyl or ethyl
  - $Z_{15}$, $Z_{16}$ and $Z_{17}$ denote, independently of one another, a $C_1$-$C_{20}$, preferably $C_1$-$C_{10}$, more particularly $C_1$-$C_4$ linear alkylene radical
  - $R_8'$ denotes a $C_6$-$C_{30}$ aryl radical, preferably phenyl
- $R_9$ denotes a linear or branched $C_1$-$C_4$ alkyl radical
- $Z_5$, $Z_6$, $Z_7$, $Z_8$, $Z_9$, $Z_{10}$ and $Z_{11}$ denote, independently of one another, a $C_1$-$C_{20}$ linear alkylene radical
- Q denotes a ring containing six members which is saturated or unsaturated and optionally comprises one or more heteroatoms
- Y, identical or different at each occurrence, represents an oxygen atom, a sulphur atom or an NH group
- h is 0, 1, 2, 3, 4 or 5
- i is 0 or 1
- j is 0, 1, 2 or 3
- k is 0 or 1
- m is 0 or 1
- n is 0 or 1
- p is 0 or 1
- q is 0 or 1
- r is 0, 1, 2 or 3
- s is 0 or 1
- t is 1 or 2
- preferably at least one of the coefficients h, i, j, k, m, n, p, q, r, s and t is non-zero, and even more preferably at least one of the coefficients i, j, k, m, n, p, r, and s is non-zero
- a represents the bond to the silicon atom
- b represents the bond to the nitrogen atom of the amino group,
a second composition comprising one or more oxidizing agents.

Likewise provided is a composition having a water content of less than 10% by weight and comprising one or more amino silicon compounds of formula (I) above and one or more fatty substances.

The invention further provides a multiple-compartment device comprising in at least one compartment a composition as previously, and in at least one other compartment an oxidizing composition.

Other features and advantages of the invention will emerge more clearly from a reading of the description and examples which follow.

In the text below, unless indicated otherwise, the end points of a range of values are included in that range.

The human keratin fibres treated by the method according to the invention are preferably the hair.

In a variant, the composition has a water content of less than 2% by weight, and preferably less than 1% by weight, relative to the weight of said composition.

In this latter case, the composition is then said to be substantially anhydrous. It should be noted that the water in question is more particularly bound water, such as water of crystallization in salts, or traces of water absorbed by the raw materials used in the production of the compositions according to the invention.

It is also specified that, in view of the use to which it is put, the composition according to the invention does not include ingredients which would make it ineligible for use in the colouring and/or lightening of human keratinous fibres. Accordingly, the ingredients it comprises are cosmetically acceptable.

As indicated above, the anhydrous composition (first composition) used in the process according to the invention comprises one or more aminosilicon compounds of formula (I).

In the formula (I), $R_1$ and $R_2$ are preferably identical.

According to one particularly advantageous embodiment, the compound of formula (I) contains only one silicon atom.

Examples of compounds of formula (I) that are suitable for the implementation of the invention include the following compounds:

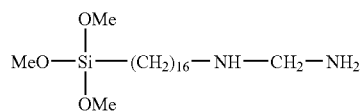
914384-34-2
Methanediamine, N-[16-(trimethoxysilyl)hexadecyl]-
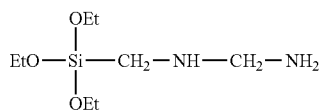
914384-32-0
Methanediamine, N-[(triethoxysilyl)methyl]-
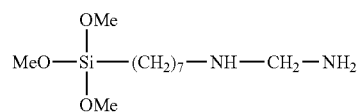
914384-30-8
Methanediamine, N-[7-(trimethoxysilyl)heptyl]-
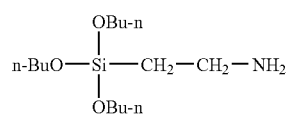
894393-40-9
Ethanamine, 2-(tributoxysilyl)-
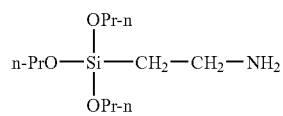
894393-33-0
Ethanamine, 2-(tripropoxysilyl)-
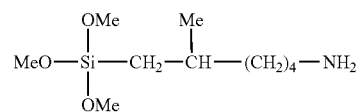
852566-95-1
1-Hexanamine, 5-methyl-6-(trimethoxysilyl)-
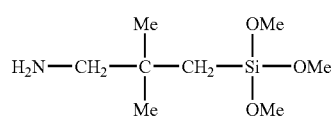
848941-45-7
1-Propanamine, 2,2-dimethyl-3-(trimethoxysilyl)-
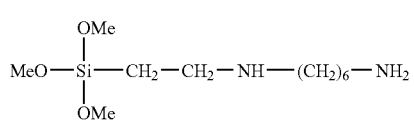
847256-03-5
1,6-Hexanediamine, N-[2-(trimethoxysilyl)ethyl]-

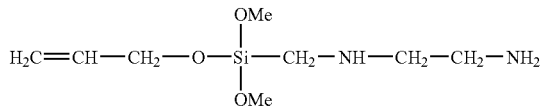

802985-77-9
1,2-Ethanediamine, N-[[dimethoxy(2-propenyloxy)silyl]methyl]

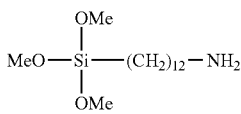

771581-51-2
1-Dodecanamine, 12-(trimethoxysilyl)-

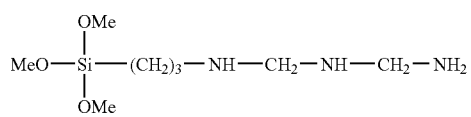

750589-52-7
Methanediamine, N-(aminomethyl)-N'-[3-(trimethoxysilyl)propyl]

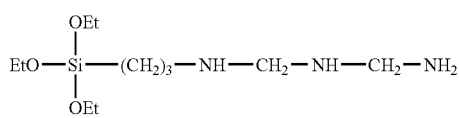

750589-50-5
Methanediamine, N-(aminomethyl)-N'-[3-(triethoxysilyl)propyl]

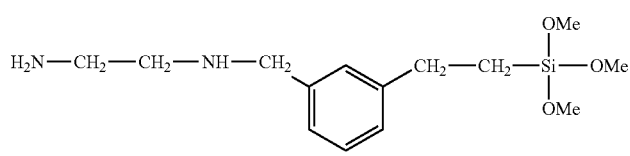

741264-27-7
1,2-Ethanediamine, N-[[3-[2-(trimethoxysilyl)ethyl]phenyl]methyl]-

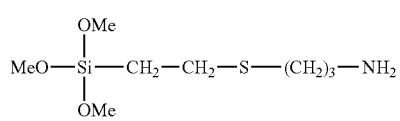

694459-23-9
1-Propanamine, 3-[[2-(trimethoxysilyl)ethyl]thio]-

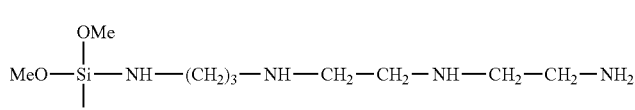

680220-31-9
1,3-Propanediamine, N-[2-[(2-aminoethyl)amino]ethyl]-N'-(trimethoxysilyl)-

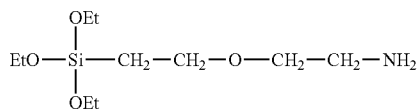
674778-27-9
Ethanamine, 2-[2-(triethoxysilyl)ethoxy]-
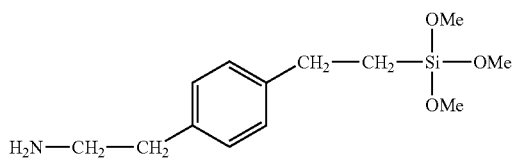
674776-80-8
Benzeneethanamine, 4-[2-(trimethoxysilyl)ethyl]
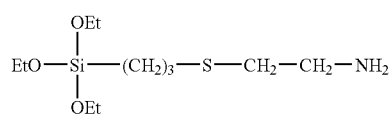
673500-46-4
Ethanamine, 2-[[3-(triethoxysilyl)propyl]thio]
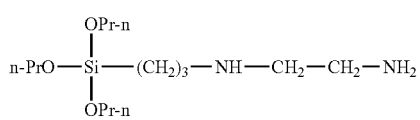
3069-23-6
N-[3-(Tripropoxysilyl)propyl]
ethylenediamine
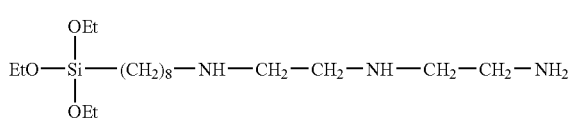
656255-27-5
1,2-Ethanediamine, N-(2-aminoethyl)-N'-[8-(triethoxysilyl)octyl]-
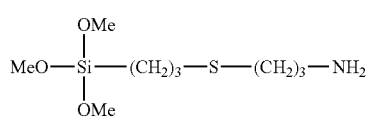
634192-74-8
1-Propanamine, 3-[[3-(trimethoxysilyl)propyl]
thio]-
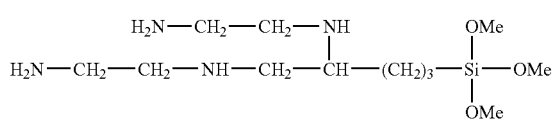
618456-93-2
1,2-Pentanediamine, N,N'-bis(2-aminoethyl)-5-(trimethoxysilyl)-

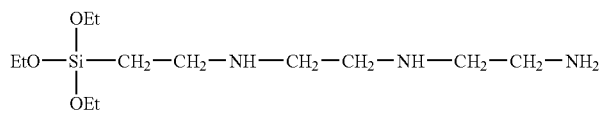

607335-14-8
1,2-Ethanediamine, N-(2-aminoethyl)-N'-[2-(triethoxysilyl)ethyl]-

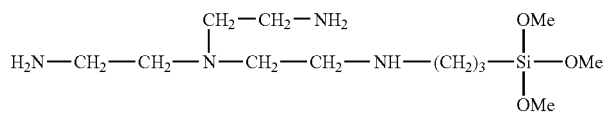

610323-36-9
1,2-Ethanediamine, N,N-bis(2-aminoethyl)-N'-[3-(trimethoxysilyl)propyl]-

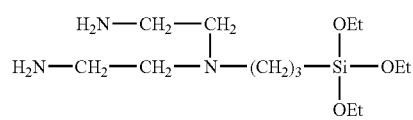

603111-49-5
1,2-Ethanediamine, N-(2-aminoethyl)-N-[3-(triethoxysilyl)propyl]-

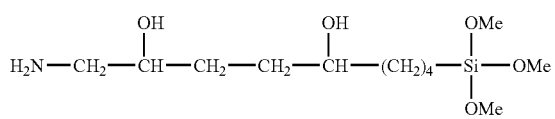

587877-12-1
2,5-Nonanediol, 1-amino-9-(trimethoxysilyl)-

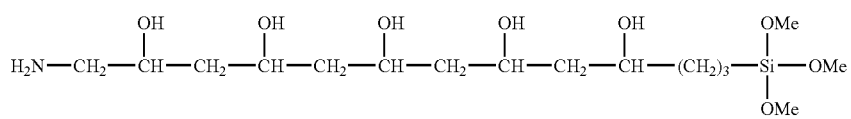

587877-24-5
2,4,6,8,10-Tridecanepentol, 1-amino-13-(trimethoxysilyl)

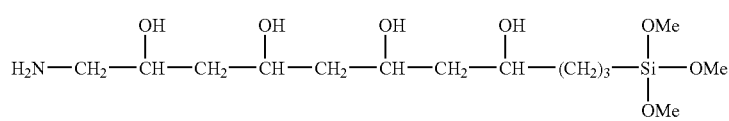

587877-22-3
2,4,6,8-Undecanetetrol, 1-amino-11-(trimethoxysilyl)

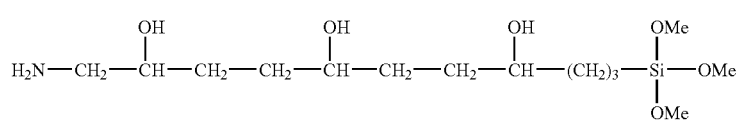

587877-14-3
2,5,8-Undecanetriol, 1-amino-11-(trimethoxysilyl)-

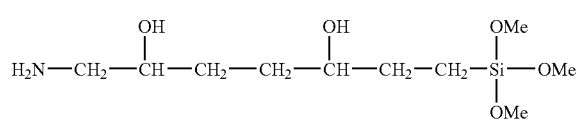

587877-10-9
2,5-Heptanediol, 1-amino-7-(trimethoxysilyl)-

-continued
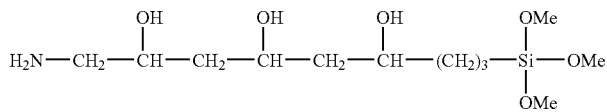
587877-08-5
2,4,6-Nonanetriol, 1-amino-9-
(trimethoxysilyl)-
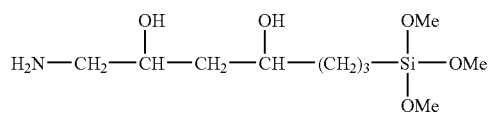
587877-06-3
2,4-Heptanediol, 1-amino-7-
(trimethoxysilyl)-
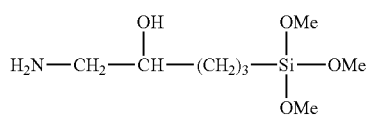
587877-04-1
2-Pentanol, 1-amino-5-
(trimethoxysilyl)-
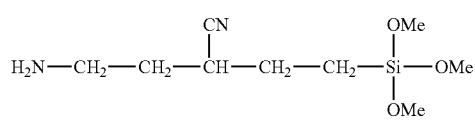
587876-76-4
Butanenitrile, 2-(2-
aminoethyl)-4-
(trimethoxysilyl)
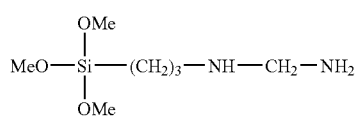
3069-20-3
N-Aminomethyl-3-
aminopropyltrimethoxysilane
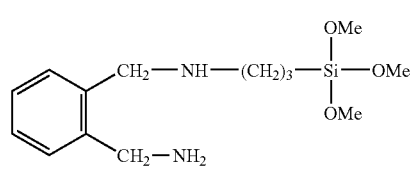
497953-03-4
1,2-Benzenedimethanamine, N-
[3-(trimethoxysilyl)propyl]
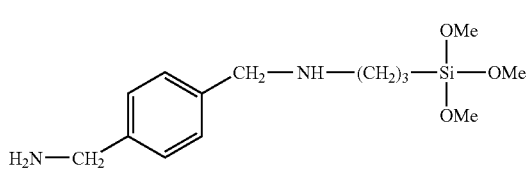
479588-79-9
1,4-Benzenedimethanamine, N-
[3-(trimethoxysilyl)propyl]

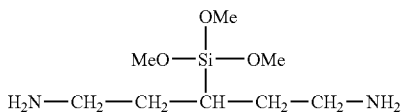
477352-07-1
1,5-Pentanediamine, 3-
(trimethoxysilyl)
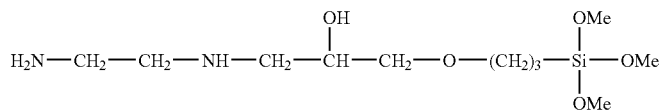
474124-35-1
2,7-Dioxa-11-aza-3-
silatridecan-9-ol, 13-amino-
3,3-dimethoxy
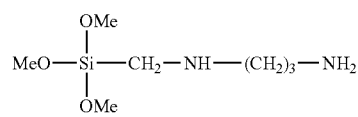
468055-31-4
1,3-Propanediamine, N-
[(trimethoxysilyl)methyl]-
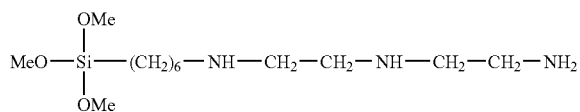
449163-54-6
1,2-Ethanediamine, N-(2-
aminoethyl)-N'-[6-
(trimethoxysilyl)hexyl]-
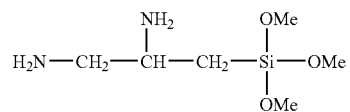
402790-28-7
1,2-Propanediamine, 3-
(trimethoxysilyl)-
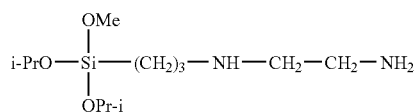
368424-33-3
1,2-Ethanediamine, N-[3-
[methoxybis(1-
methylethoxy)silyl]propyl]-
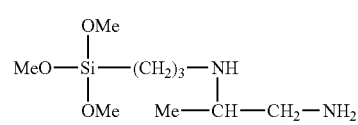
366001-46-9
1,2-Propanediamine, N2-[3-
(trimethoxysilyl)propyl]-

-continued
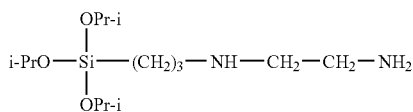
355410-25-2
1,2-Ethanediamine, N-[3-
[tris(1-
methylethoxy)silyl]propyl]-
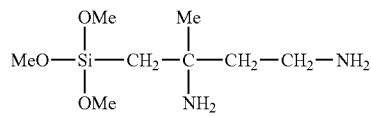
331443-68-6
1,3-Butanediamine, 3-methyl-
4-(trimethoxysilyl)-
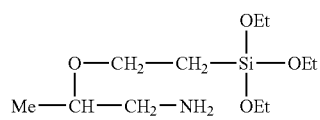
327024-70-4
1-Propanamine, 2-[2-
(triethoxysilyl)ethoxy]-
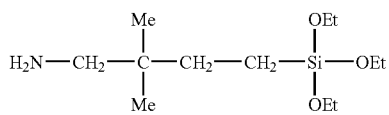
327024-67-9
4-Amino-3,3-
dimethylbutyltriethoxysilane
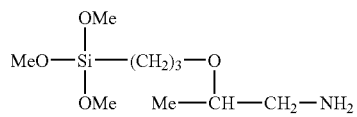
327024-66-8
1-Propanamine, 2-[3-
(trimethoxysilyl)propoxy]-
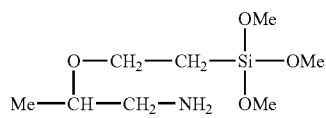
327024-65-7
1-Propanamine, 2-[2-
(trimethoxysilyl)ethoxy]-
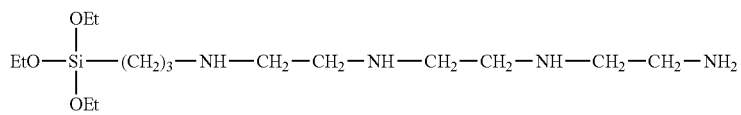
299199-34-1
1,2-Ethanediamine, N-(2-aminoethyl)-N'-[2-[[3-
(triethoxysilyl)propyl]amino]ethyl]

-continued
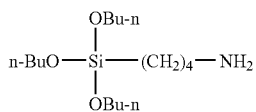
314733-26-1
1-Butanamine, 4-(tributoxysilyl)-
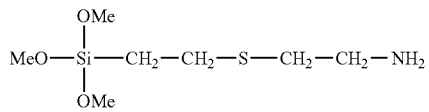
287184-57-0
Ethanamine, 2-[[2-(trimethoxysilyl)ethyl]thio]
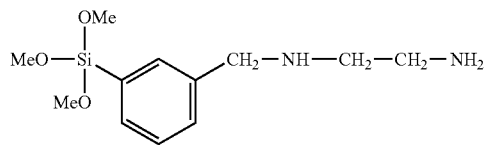
256399-63-0
1,2-Ethanediamine, N-[[3-(trimethoxysilyl)phenyl]methyl]
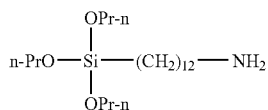
253596-69-9
1-Dodecanamine, 12-(tripropoxysilyl)
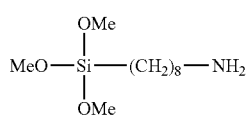
253596-68-8
1-Octanamine, 8-(trimethoxysilyl)
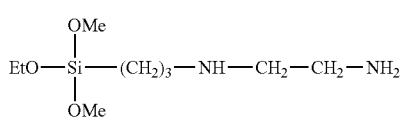
224789-93-9
1,2-Ethanediamine, N-[3-(ethoxydimethoxysilyl)propyl]
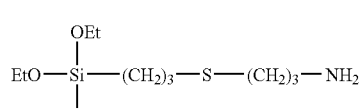
208463-57-4
1-Propanamine, 3-[[3-(triethoxysilyl)propyl]thio]

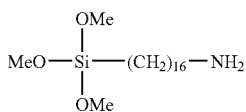
193157-95-8
16-Aminohexadecyltrimethoxy silane
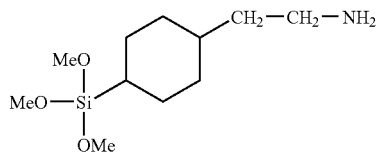
188548-64-3
Cyclohexaneethanamine, 4-(trimethoxysilyl)
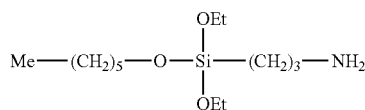
183235-71-4
3-[Diethoxy(hexyloxy)silyl]-1-propanamine
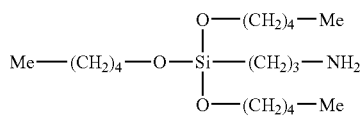
180896-30-4
3-[Tris(pentyloxy)silyl]-1-propanamine
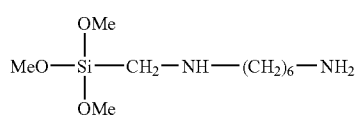
172684-43-4
1,6-Hexanediamine, N-[(trimethoxysilyl)methyl]-
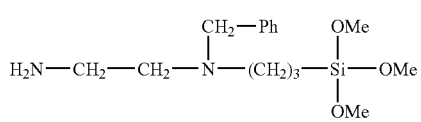
169873-94-3
1,2-Ethanediamine, N-(phenylmethyl)-N-[3-(trimethoxysilyl)propyl]-
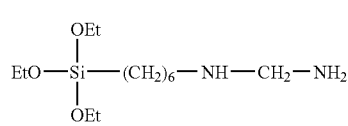
167318-83-4
Methanediamine, N-[6-(triethoxysilyl)hexyl]-

-continued
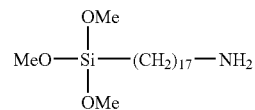
163193-89-3
(17-Aminoheptadecyl)trimethoxysilane
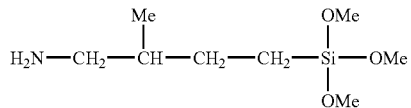
157923-78-9
4-Amino-3-methylbutyltrimethoxysilane
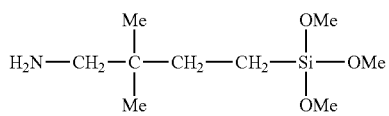
157923-74-5
4-(Trimethoxysilyl)-2,2-dimethylbutanamine
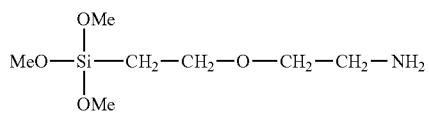
156212-74-7
Ethanamine, 2-[2-(trimethoxysilyl)ethoxy]
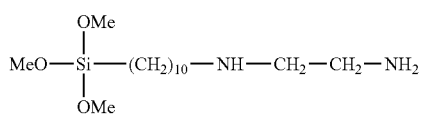
144006-72-4
1,2-Ethanediamine, N-[10-(trimethoxysilyl)decyl]-
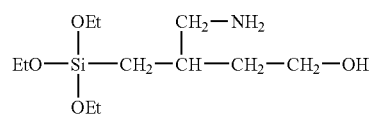
143203-42-3
1-Butanol, 3-(aminomethyl)-4-(triethoxysilyl)
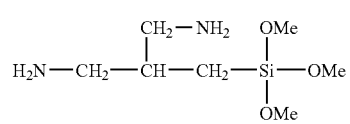
138249-35-1
1,3-Propanediamine, 2-[(trimethoxysilyl)methyl]

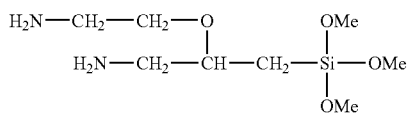
136398-53-3
1-Propanamine, 2-(2-aminoethoxy)-3-(trimethoxysilyl)
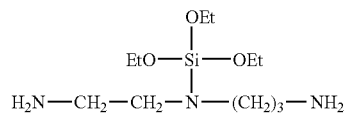
135702-44-2
1,3-Propanediamine, N-(2-aminoethyl)-N-(triethoxysilyl)
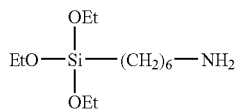
134821-45-7
1-Hexanamine, 6-(triethoxysilyl)-
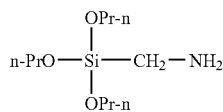
131535-65-4
Methanamine, 1-(tripropoxysilyl)-
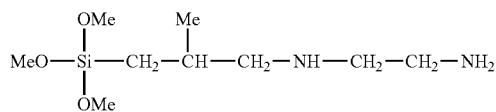
2530-82-7
1,2-Ethanediamine, N-[2-methyl-3-(trimethoxysilyl)propyl]-
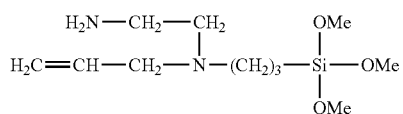
127675-82-5
1,2-Ethanediamine, N-2-propenyl-N-[3-(trimethoxysilyl)propyl]-
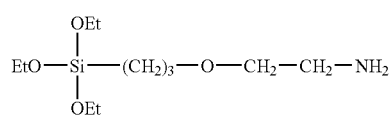
126552-43-0
2-[3-(Triethoxysilyl)propoxy]ethylamine

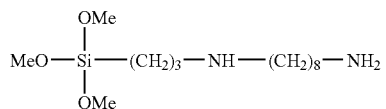
124008-17-9
1,8-Octanediamine, N-[3-(trimethoxysilyl)propyl]-
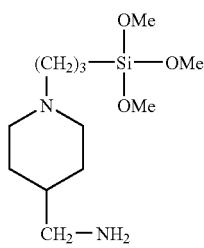
123150-57-2
4-Piperidinemethanamine, 1-[3-(trimethoxysilyl)propyl]
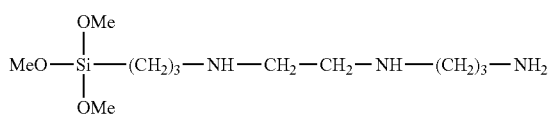
121487-64-7
1,3-Propanediamine, N-[2-[[3-(trimethoxysilyl)propyl]amino]ethyl]-
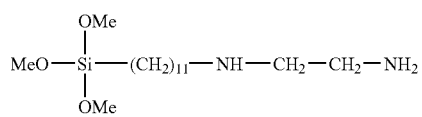
121772-92-7
1,2-Ethanediamine, N-[11-(trimethoxysilyl)undecyl]-
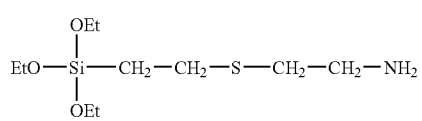
120615-58-9
Ethanamine, 2-[[2-(triethoxysilyl)ethyl]thio]-
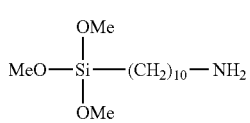
120183-15-5
(10-Aminodecyl)trimethoxysilane
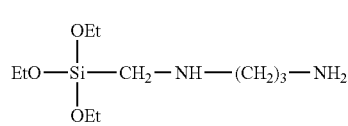
119170-83-1
1,3-Propanediamine, N-[(triethoxysilyl)methyl]-

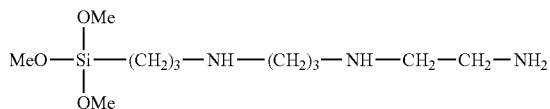
118746-32-0
1,3-Propanediamine, N-(2-aminoethyl)-N'-[3-(trimethoxysilyl)propyl]
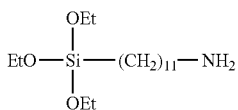
116821-45-5
11-(Aminoundecyl)triethoxysilane
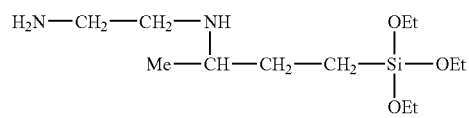
108737-18-4
1,2-Ethanediamine, N-[1-methyl-3-(triethoxysilyl)propyl]
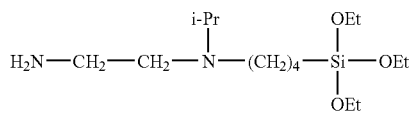
106894-51-3
1,2-Ethanediamine, N-(1-methylethyl)-N-[4-(triethoxysilyl)butyl]
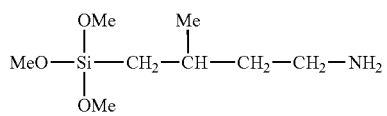
106890-59-9
1-Butanamine, 3-methyl-4-(trimethoxysilyl)
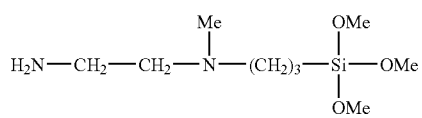
104472-59-5
1,2-Ethanediamine, N-methyl-N-[3-(trimethoxysilyl)propyl]-
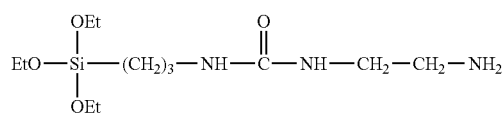
104261-39-4
Urea, N-(2-aminoethyl)-N'-[3-(triethoxysilyl)propyl]

-continued
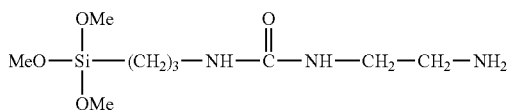
104261-38-3
Urea, N-(2-aminoethyl)-N'-[3-
(trimethoxysilyl)propyl]
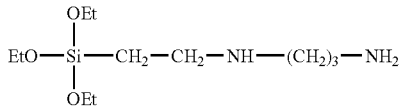
104230-83-3
1,3-Propanediamine, N-[2-
(triethoxysilyl)ethyl]-
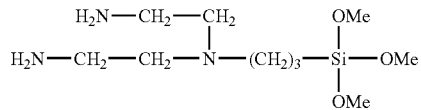
103526-27-8
N,N-Di(2-aminoethyl)-3-
aminopropyltrimethoxysilane
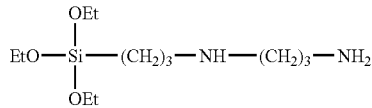
99740-25-7
1,3-Propanediamine, N-[3-
(triethoxysilyl)propyl]-
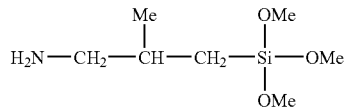
99503-87-4
1-Propanamine, 2-methyl-3-
(trimethoxysilyl)-
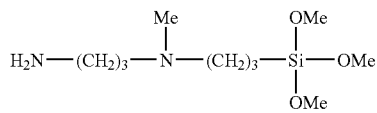
97040-35-2
1,3-Propanediamine, N-
methyl-N-[3-
(trimethoxysilyl)propyl]-
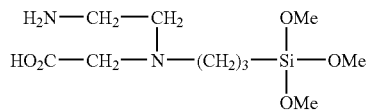
95017-24-6
Glycine, N-(2-aminoethyl)-N-
[3- (trimethoxysilyl)propyl]

-continued
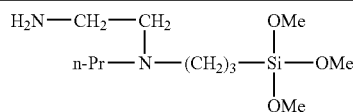
95017-23-5
1,2-Ethanediamine, N-propyl-
N-[3-
(trimethoxysilyl)propyl]-
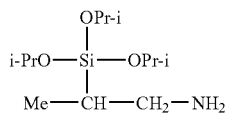
94989-07-8
1-Propanamine, 2-[tris(1-
methylethoxy)silyl]-
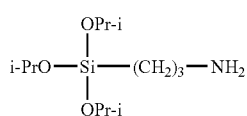
94989-06-7
3-Aminopropyltriisopropoxy
silane
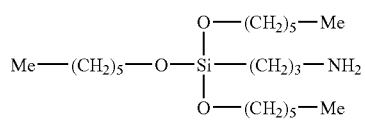
94277-92-6
3-[Tris(hexyloxy)silyl]-1-
propanamine
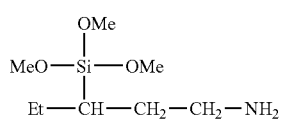
92116-16-0
3-(Trimethoxysilyl)-1-
pentanamine
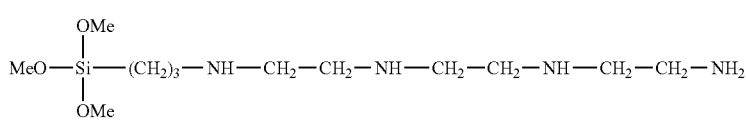
84271-30-7
N-(2-Aminoethyl)-N'-[2-[[3-
(trimethoxysilyl)propyl]amino]ethyl]-1,2-ethanediamine
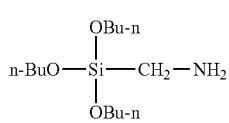
84869-17-0
Aminomethyltributoxysilane
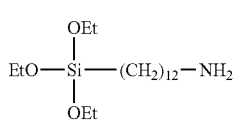
83943-65-1
1-Dodecanamine, 12-
(triethoxysilyl)

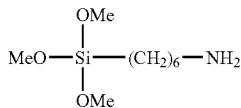
83943-64-0
1-Hexanamine, 6-(trimethoxysilyl)
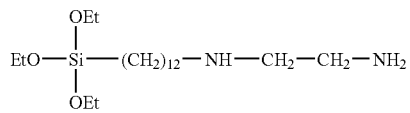
83943-61-7
1,2-Ethanediamine, N-[12-(triethoxysilyl)dodecyl]
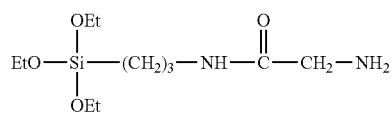
76444-79-6
Acetamide, 2-amino-N-[3-(triethoxysilyl)propyl]-
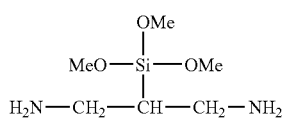
75522-79-1
1,3-Propanediamine, 2-(trimethoxysilyl)-
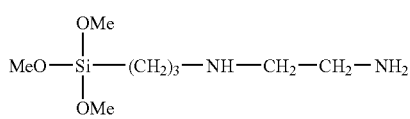
1760-24-3
3-(2-Aminoethyl)aminopropyl trimethoxysilane
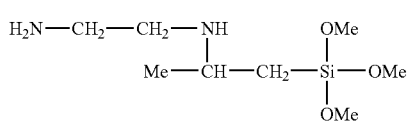
71408-50-9
1,2-Ethanediamine, N-[1-methyl-2-(trimethoxysilyl)ethyl]
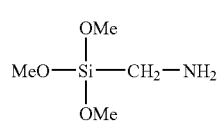
71408-48-5
Methanamine, 1-(trimethoxysilyl)-

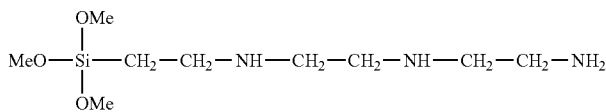
69659-08-1
1,2-Ethanediamine, N-(2-aminoethyl)-N'-[2-(trimethoxysilyl)ethyl]-
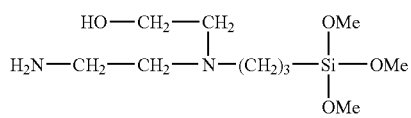
69465-81-2
Ethanol, 2-[(2-aminoethyl)[3-(trimethoxysilyl)propyl]amino]-
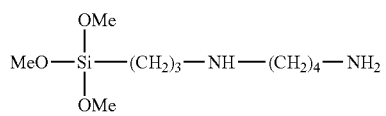
69465-80-1
1,4-Butanediamine, N-[3-(trimethoxysilyl)propyl]-
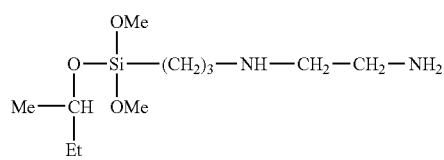
69465-78-7
1,2-Ethanediamine, N-[3-[dimethoxy(1-methylpropoxy)silyl]propyl]-
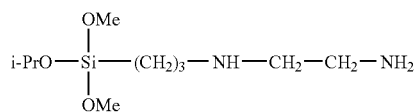
69465-77-6
1,2-Ethanediamine, N-[3-[dimethoxy(1-methylethoxy)silyl]propyl]-
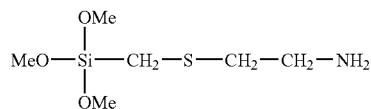
65834-03-9
Ethanamine, 2-[[(trimethoxysilyl)methyl]thio]-
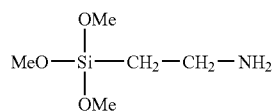
65644-31-7
2-(Trimethoxysilyl)ethylamine

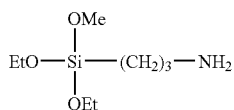
61083-96-3
1-Propanamine, 3-(diethoxymethoxysilyl)-
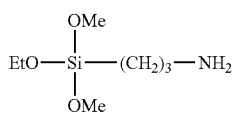
61083-95-2
1-Propanamine, 3-(ethoxydimethoxysilyl)
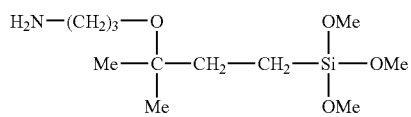
59025-07-9
[3-(3-Aminopropoxy)-3,3-dimethylpropyl]trimethoxy silane
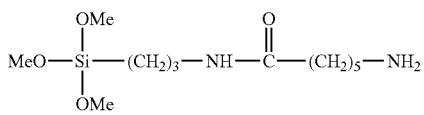
58824-57-0
Hexanamide, 6-amino-N-[3-(trimethoxysilyl)propyl]
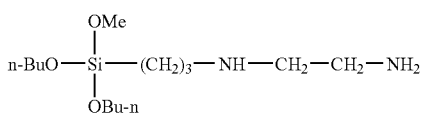
58473-37-3
1,2-Ethanediamine, N-[3-(dibutoxymethoxysilyl) propyl]
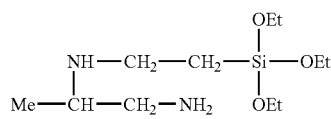
58069-00-4
1,2-Propanediamine, N2-[2-(triethoxysilyl)ethyl]
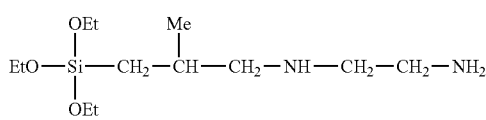
56541-78-7
1,2-Ethanediamine, N-[2-methyl-3-(triethoxysilyl)propyl]

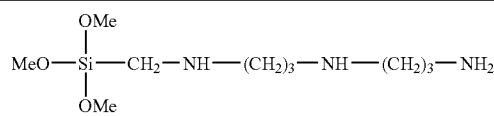
56539-73-2
N-Trimethoxysilylmethyl
dipropylenetriamine
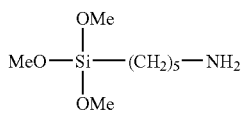
54894-82-5
1-Pentanamine, 5-
(trimethoxysilyl)-
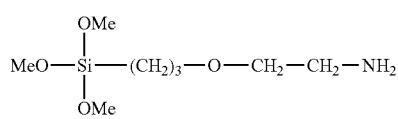
54572-92-8
Ethanamine, 2-[3-
(trimethoxysilyl)propoxy]-
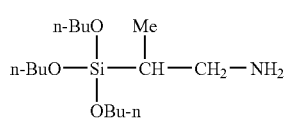
53813-14-2
1-Propanamine, 2-
(tributoxysilyl)-
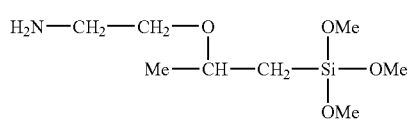
52469-27-9
Ethanamine, 2-[1-methyl-2-
(trimethoxysilyl)ethoxy]-
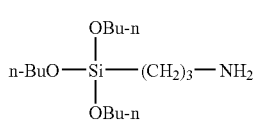
52340-01-9
1-Propanamine, 3-
(tributoxysilyl)-
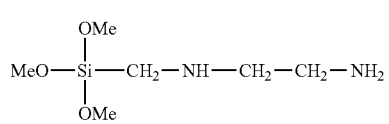
51980-40-6
N-[(Trimethoxysilyl)methyl]
ethylenediamine
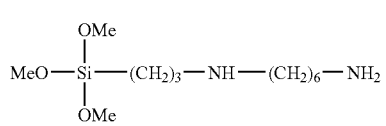
51895-58-0
3-(6-Aminohexyl)aminopropyl
trimethoxysilane -continued
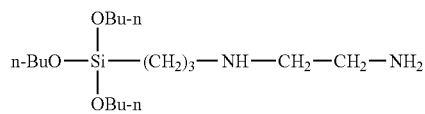
51895-55-7
N-[3-(Tributoxysilyl)propyl]
ethylenediamine
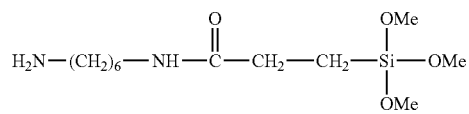
51833-30-8
N-(6-
Aminohexyl)trimethoxysilyl
carboxamide
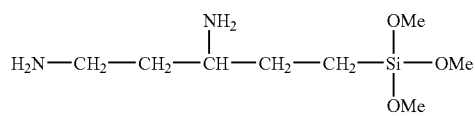
51279-08-4
1,3-Pentanediamine, 5-
(trimethoxysilyl)-
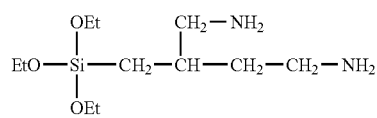
51279-07-3
1,4-Butanediamine, 2-
[(triethoxysilyl)methyl]-
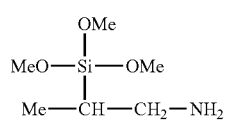
50602-95-4
1-Propanamine, 2-
(trimethoxysilyl)-
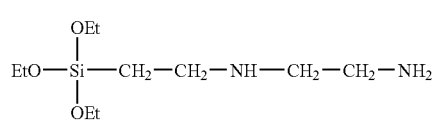
45168-85-2
[2-(2-Aminoethylamino)ethyl]
triethoxysilane
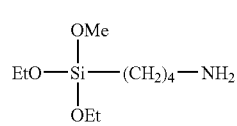
45116-10-7
1-Butanamine, 4-
(diethoxymethoxysilyl)-

-continued
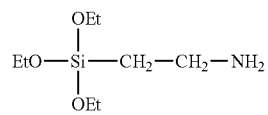
45074-31-5
2-Aminoethyltriethoxysilane
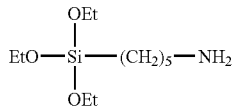
1067-48-7
1-Pentanamine, 5-
(triethoxysilyl)-
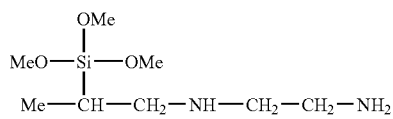
42346-52-1
1,2-Ethanediamine, N-[2-
(trimethoxysilyl)propyl]
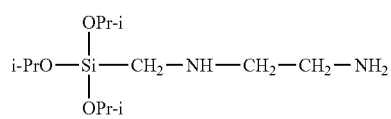
42258-59-3
N-(Triisopropoxysilylmethyl)
ethylenediamine
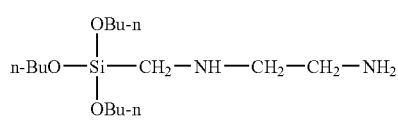
42040-66-4
N-(Tributoxysilylmethyl)
ethylenediamine
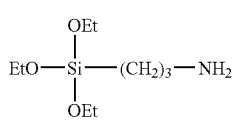
919-30-2
3-Aminopropyltriethoxysilane
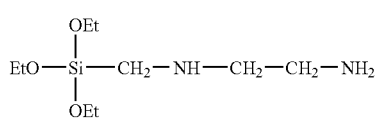
41555-92-4
N-(Triethoxysilylmethyl)
ethylenediamine
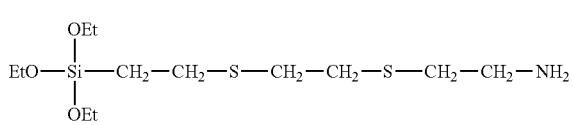
41051-81-4
3,6-Dithia-8-
aminotriethoxysilane -continued
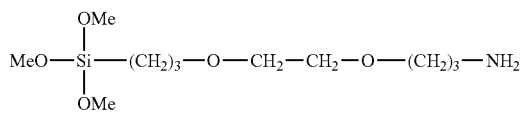
40762-36-5
4,7-Dioxa-10-aminodecyltrimethoxysilane
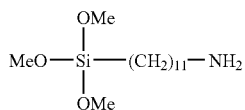
40762-31-0
11-Aminoundecyltrimethoxysilane
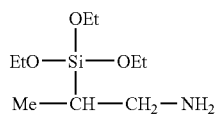
36957-84-3
(2-Aminoisopropyl)triethoxy
silane
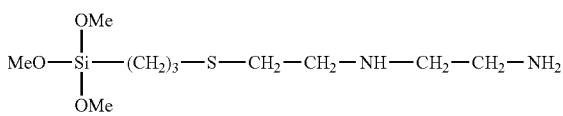
35514-63-7
1,2-Ethanediamine, N-[2-[[3-(trimethoxysilyl)propyl]thio]ethyl]-
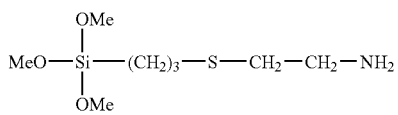
35514-61-5
3-Trimethoxypropylthioethyl
amine
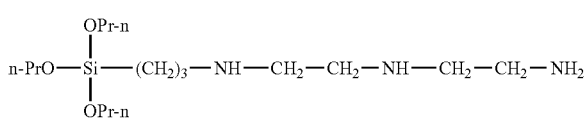
30652-34-7
Diethylenetriamine, 1-[3-(tripropoxysilyl)propyl]
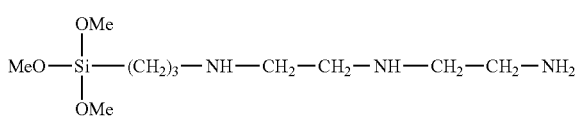
35141-30-1
4,7,10-Triazadecyltrimethoxysilane
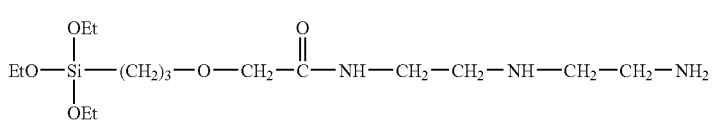
26440-73-3
Acetamide, N-[2-[(2-aminoethyl)amino]ethyl]-2-[3-(triethoxysilyl)propoxy]-

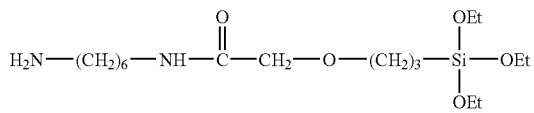
26440-74-4
Acetamide, N-(6-aminohexyl)-
2-[3-(triethoxysilyl)propoxy]
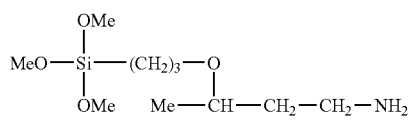
26092-76-2
Butylamine, 3-[3-
(trimethoxysilyl)propoxy]-
(8CI)
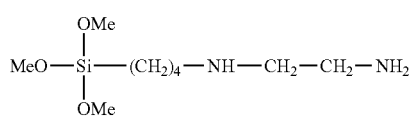
25491-73-0
1,2-Ethanediamine, N-[4-
(trimethoxysilyl)butyl]-
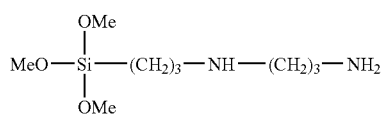
25147-91-5
3-[(3-
Aminopropyl)amino]propyl
trimethoxysilane
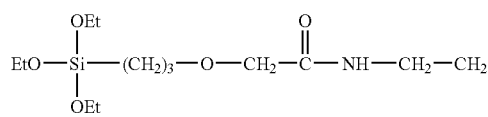
25130-84-1
Acetamide, N-(2-aminoethyl)-
2-[3-
(triethoxysilyl)propoxy]-
(8CI) (CA
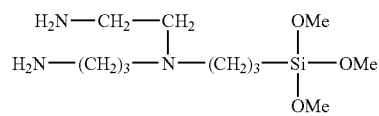
24763-39-1
1,3-Propanediamine, N-(2-
aminoethyl)-N-[3-
(trimethoxysilyl)propyl]
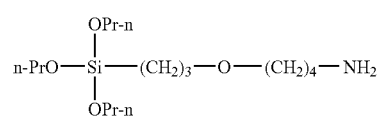
23386-49-4
Butylamine, 4-[3-
(tripropoxysilyl)propoxy]

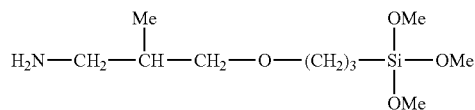
23386-47-2
3-(2-Methyl-3-aminopropoxy)propyltrimethoxy silane
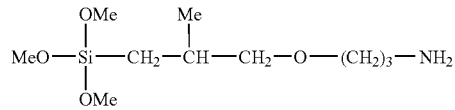
23386-46-1
Propylamine, 3-[2-methyl-3-(trimethoxysilyl)propoxy]
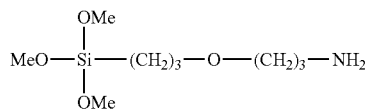
23386-45-0
3-[3-(Trimethoxysilyl)propoxy]propylamine
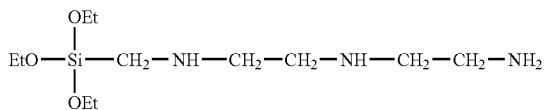
23021-89-8
1,2-Ethanediamine, N-(2-aminoethyl)-N'-[(triethoxysilyl)methyl]-
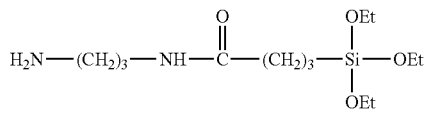
18551-50-3
Butyramide, N-(3-aminopropyl)-4-(triethoxysilyl)
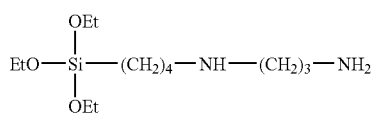
18418-52-5
1,3-Propanediamine, N-[4-(triethoxysilyl)butyl]
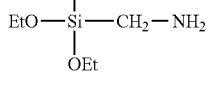
18306-83-7
Aminomethyltriethoxysilane -continued
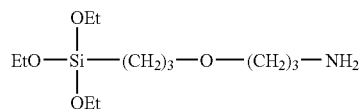
18082-90-1
(3-Aminopropoxy)propyl
triethoxysilane
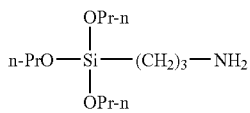
18082-68-3
1-Propanamine, 3-
(tripropoxysilyl)
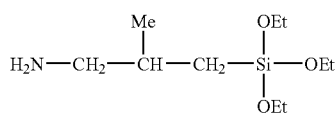
17961-40-9
1-Propanamine, 2-methyl-3-
(triethoxysilyl)-
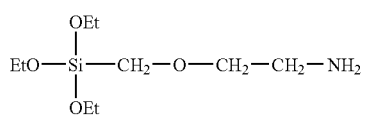
17886-99-6
2-[(Triethoxysilyl)methoxy]
ethylamine
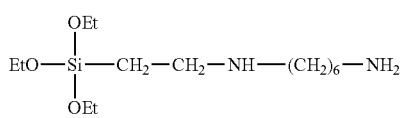
17576-02-2
1,6-Hexanediamine, N-[2-
(triethoxysilyl)ethyl]
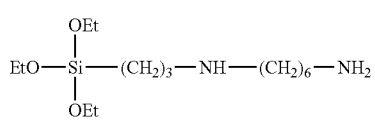
15484-16-9
1,6-Hexanediamine, N-[3-
(triethoxysilyl)propyl]
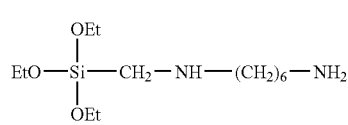
15129-36-9
N-[(Triethoxysilyl)methyl]-
1,6-hexanediamine
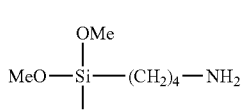
15005-59-1
(4-
Aminobutyl)trimethoxysilane -continued
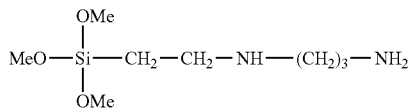
14513-31-6
1,3-Propanediamine, N-[2-
(trimethoxysilyl)ethyl]
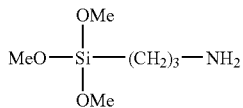
13822-56-5
(3-
Aminopropyl)trimethoxysilane
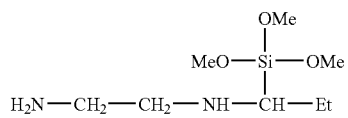
13170-53-1
1,2-Ethanediamine, N-[1-
(trimethoxysilyl)propyl]
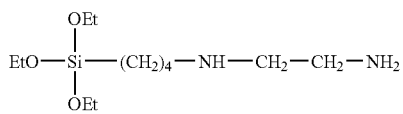
13081-59-9
1,2-Ethanediamine, N-[4-
(triethoxysilyl)butyl]
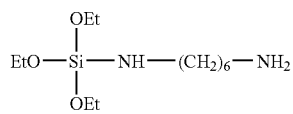
10446-40-9
1,6-Hexanediamine, N-
(triethoxysilyl)
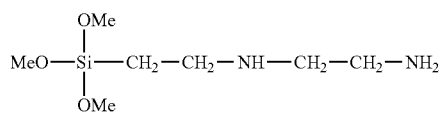
7719-00-8
2-Amino-2'-(trimethoxysilyl)
diethylamine
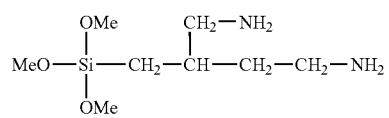
6037-49-6
1,4-Butanediamine, 2-
[(trimethoxysilyl)methyl]

-continued

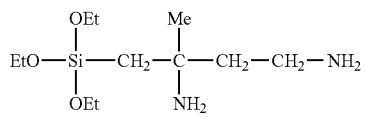

5888-01-7
1,3-Butanediamine, 3-methyl-
4-(triethoxysilyl)

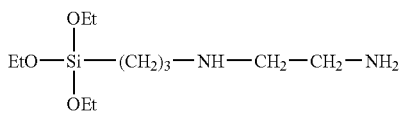

5089-72-5
3-(2-Aminoethylamine)propyl
triethoxysilane

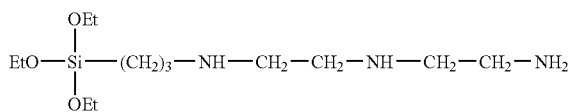

4693-51-0
Diethylenetriamine, 1-[3-
(triethoxysilyl)propyl]

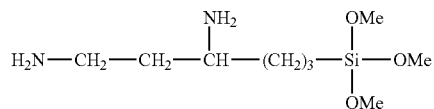

4543-14-0
1,3-Hexanediamine, 6-
(trimethoxysilyl)

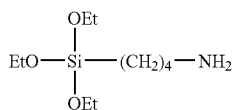

3069-30-5
4-Aminobutyltriethoxysilane

The compounds of formula (I) preferably comprise at least one silicon atom bearing three alkoxy or alkenyloxy groups.

In the formula (I), $R_1$ and $R_2$ are preferably identical.

According to another variant, $R_1$, $R_2$ and $R_3$ are identical.

In accordance with one advantageous embodiment, the coefficients k, n and s denote 0.

According to one particularly advantageous embodiment, the compound of formula (I) comprises only one silicon atom.

According to one variant of the invention, the compounds of formula (I) contain only one silicon atom bearing three $C_1$-$C_4$ alkoxy groups.

According to this variant, $R_1$, $R_2$ and $R_3$ are preferably identical.

In accordance with one advantageous embodiment of this same variant, the coefficients k, n and s denote more particularly 0; and p is 1.

In accordance with an even more preferred embodiment, the compounds of formula (I) corresponding to the preferred criteria of the variant detailed before are such that, in addition, the coefficients r, j and m are zero. With particular advantage, the compounds of formula (I) which correspond to this variant are such that i is also zero.

According to one very advantageous embodiment of the invention, the compound of formula (I) is (3-aminopropyl) triethoxysilane.

Typically the amount of compound of formula (I) represents from 0.1% to 50% and preferably from 1% to 30% by weight, relative to the weight of the first composition.

The composition comprising the aminosilicon compound(s) of formula (I) may also comprise one or more oxidation dye precursors, more particularly one or more oxidation bases optionally in combination with one or more couplers, one or more direct dyes, or mixtures thereof.

By way of example, the oxidation bases are selected from para-phenylenediamines, bis(phenyl)-alkylenediamines, para-aminophenols, ortho-aminophenols and heterocyclic bases, and the addition salts thereof.

Among the para-phenylenediamines that may be mentioned, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloro-aniline, 2-β-hydroxyethyl-para-phenylenediamine, 2-fluoro-paraphenylenediamine, 2-isopropyl-para-phenyl-enediamine, N-(β-hydroxypropyl)-para-phenylenediamine, 2-hydroxymethyl-para-phenylenediamine, N,N-dimethyl-3-methyl-para-phenylenediamine, N,N-(ethyl, β-hydroxy-ethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxy-ethyloxy-para-phenylenediamine, 2-β-acetylaminoethyl-oxy-para-phenylenediamine, N-(β-methoxyethyl)-para-phenylenediamine, 4-aminophenylpyrrolidine, 2-thienyl-para-phenylenediamine, 2-β-hydroxyethylamino-5-amino-toluene and 3-hydroxy-1-(4'-aminophenyl)pyrrolidine, and the addition salts thereof with an acid.

Among the para-phenylenediamines mentioned above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylene-diamine, N,N'-bis(4-aminophenyl)tetramethylenediamine, N,N'-bis(β-hydroxyethyl)-N,N'-bis(4-aminophenyl) tetra-methylenediamine, N,N'-bis(4-methylaminophenyl)tetra-methylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases that may be mentioned, for example, are pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-amino-pyridine and 3,4-diaminopyridine, and the addition salts thereof.

Other pyridine oxidation bases that are useful in the present invention are the 3-aminopyrazolo[1,5-a]-pyridine oxidation bases or addition salts thereof described, for example, in patent application FR 2 801 308. Examples that may be mentioned include pyrazolo[1,5-a]pyrid-3-ylamine, 2-acetylaminopyrazolo-[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-yl-amine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-yl-pyrazolo[1,5-a]pyrid-3-ylamine, pyrazolo[1,5-a]-pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo-[1,5-a]pyrid-7-yl)(2-hydroxyethyl)amino]ethanol, 3-aminopyrazolo[1,5-a]pyridin-5-ol, 3-aminopyrazolo-[1,5-a]pyridin-4-ol, 3-aminopyrazolo[1,5-a]pyridin-6-ol and 3-aminopyrazolo[1,5-a]pyridin-7-ol, and the addition salts thereof.

Among the pyrimidine derivatives that may be mentioned are the compounds described, for example, in patents DE 2 359 399; JP 88-169 571; JP 05-63124; EP 0 770 375 or patent application WO 96/15765, for instance 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triamino-pyrimidine, and the addition salts thereof, and the tautomeric forms thereof, when a tautomeric equilibrium exists.

Among the pyrazole derivatives that may be mentioned are the compounds described in patents DE 3 843 892 and DE 4 133 957, and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)-pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazino-pyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)-pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triamino-pyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof. 4,5-diamino-1-(β-methoxyethyl)pyrazole may also be used.

The composition may optionally comprise one or more couplers advantageously selected from those conventionally used for the colouring of keratin fibres.

Among these couplers, mention may be made especially of meta-phenylenediamines, meta-amino-phenols, meta-diphenols, naphthalenic couplers and heterocyclic couplers, and also the addition salts thereof.

Mention may be made, for example, of 1,3-dihydroxybenzene, 1,3-dihydroxy-2-methylbenzene, 4-chloro-1,3-dihydroxybenzene, 2,4-diamino-1-(β-hydroxy-ethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethyl-pyrazolo[1,5-b]-1,2,4-triazole, 2,6-dimethyl[3,2-c]-1,2,4-triazole and 6-methylpyrazolo[1,5-a]benzimid-azole, the addition salts thereof with an acid, and mixtures thereof.

In general, the addition salts of the oxidation bases and couplers that may be used are especially selected from the addition salts with an acid such as the hydrochlorides, hydrobromides, sulphates, citrates, succinates, tartrates, lactates, tosylates, benzenesulphonates, phosphates and acetates.

The oxidation base or bases each advantageously represent from 0.0001% to 10% by weight relative to the weight of the composition, and preferably from 0.005% to 5% by weight relative to the total weight of the composition.

The amount of coupler(s), if it is (they are) present, each advantageously represent from 0.0001% to 10% by weight relative to the weight of the composition, and preferably from 0.005% to 5% by weight relative to the total weight of the composition.

The composition with the amino silicon compound or compounds of formula (I) may optionally comprise one or more direct dyes which may be selected in particular from cationic, neutral or anionic species.

Examples of suitable direct dyes include direct azo dyes; direct methine dyes; direct carbonyl dyes; direct azine dyes; direct (hetero)aryl nitro dyes; direct tri(hetero)aryl methane dyes; porphyrins; phthalocyanines; and natural direct dyes, alone or in mixtures.

More particularly, the azo dyes comprise an —N=N— function in which the two nitrogen atoms are not simultaneously engaged in a ring. However, it is not excluded for one of the two nitrogen atoms of the sequence —N=N— to be engaged in a ring.

The dyes of the methine family are more particularly compounds comprising at least one sequence selected from >C=C< and —N=C< in which the two atoms are not simultaneously engaged in a ring. However, it is pointed out that one of the nitrogen or carbon atoms of the sequences may be engaged in a ring. More particularly, the dyes of this family are derived from compounds of methine, azomethine, mono- and diarylmethane type, indoamines (or diphenylamines), indophenols, indoanilines, carbocyanines, azacarbocyanines and their isomers, diazacarbocyanines and their isomers, tetraazacarbocyanines and hemi-cyanines.

As regards the dyes of the carbonyl family, examples that may be mentioned include dyes chosen from acridone, benzoquinone, anthraquinone, naphthoquinone, benzanthrone, anthranthrone, pyranthrone, pyrazol-anthrone, pyrimidinoanthrone, flavanthrone, idanthrone, flavone, (iso)violanthrone, isoindolinone, benzimid-azolone, isoquinolinone, anthrapyridone, pyrazolo-quinazolone, perinone, quinacridone, quinophthalone, indigoid, thioindigo, naphthalimide, anthrapyrimidine, diketopyrrolopyrrole and coumarin dyes.

As regards the dyes of the cyclic azine family, mention may be made especially of azine, xanthene, thioxanthene, fluorindine, acridine, (di)oxazine, (di)thiazine and pyronin dyes.

The nitro (hetero) aromatic dyes are more particularly nitrobenzene or nitropyridine direct dyes.

As regards the dyes of porphyrin or phthalocyanine type, it is possible to use cationic or non-cationic compounds, optionally comprising one or more metals or metal ions, for instance alkali metals, alkaline-earth metals, zinc and silicon.

Examples of particularly suitable direct dyes that may be mentioned include nitro dyes of the benzene series; azo direct dyes; azomethine direct dyes; methine direct dyes; azacarbocyanines such as tetraazacarbocyanines (tetraazapentamethines); quinone direct dyes, and in particular anthraquinone, naphthoquinone or benzoquinone dyes; azine direct dyes; xanthene direct dyes; triarylmethane direct dyes; indoamine direct dyes; indigoid direct dyes; phthalocyanine and porphyrin direct dyes, and natural direct dyes, alone or in mixtures.

These dyes may be monochromophoric dyes (i.e. comprising only one dye) or polychromophoric, preferably di- or trichromophoric, dyes; the chromophores may be identical or different, and from the same chemical family or otherwise. It should be noted that a polychromophoric dye comprises two or more radicals each derived from a molecule that absorbs in the visible region between 400 and 800 nm. Furthermore, this absorbance of the dye does not require any prior oxidation thereof, or combination with any other chemical species.

In the case of polychromophoric dyes, the chromophores are connected together by means of at least one linker, which may be cationic or non-cationic.

The linker is preferably a linear, branched or cyclic $C_1$-$C_{20}$ alkyl chain which is optionally interrupted by at least one heteroatom (such as nitrogen, oxygen) and/or by at least one group comprising such a heteroatom (CO, $SO_2$), optionally interrupted by at least one heterocycle which is or is not fused with a phenyl nucleus, and comprising at least one quaternized nitrogen atom which is part of said heterocycle, and optionally at least one other heteroatom (such as oxygen, nitrogen or sulphur), optionally interrupted by at least one substituted or unsubstituted naphthyl or phenyl group, optionally at least one quaternary ammonium group which is substituted by two optionally substituted $C_1$-$C_{15}$ alkyl groups; the linker does not contain a nitro, nitroso or peroxo group.

If the heterocycles or aromatic nuclei are substituted, they are substituted, for example, by one or more $C_1$-$C_8$ alkyl radicals which are optionally substituted by a hydroxyl group, $C_1$-$C_2$ alkoxy, $C_2$-$C_4$ hydroxyalkoxy, acetylamino, amino substituted by one or two $C_1$-$C_4$ alkyl radicals, which optionally carry at least one hydroxyl group, or the two radicals may, with the nitrogen atom to which they are attached, form a 5- or 6-membered heterocycle, optionally comprising another heteroatom identical to or different from nitrogen; a halogen atom; a hydroxyl group; a $C_1$-$C_2$ alkoxy radical; a $C_2$-$C_4$ hydroxyalkoxy radical; an amino radical; an amino radical substituted by one or two identical or different $C_1$-$C_4$ alkyl radicals which optionally carry at least one hydroxyl group.

Among the benzenic direct dyes that may be used according to the invention, mention may be made in a non-limiting manner of the following compounds:

1,4-diamino-2-nitrobenzene;
1-amino-2-nitro-4-β-hydroxyethylaminobenzene;
1-amino-2-nitro-4-bis(β-hydroxyethyl)aminobenzene;
1,4-bis(β-hydroxyethylamino)-2-nitrobenzene;
1-β-hydroxyethylamino-2-nitro-4-bis(β-hydroxyethylamino) benzene;
1-β-hydroxyethylamino-2-nitro-4-aminobenzene;
1-β-hydroxyethylamino-2-nitro-4-(ethyl) (β-hydroxyethyl)aminobenzene;
1-amino-3-methyl-4-β-hydroxyethylamino-6-nitro-benzene;
1-amino-2-nitro-4-β-hydroxyethylamino-5-chloro-benzene;
1,2-diamino-4-nitrobenzene;
1-amino-2-β-hydroxyethylamino-5-nitrobenzene;
1,2-bis(β-hydroxyethylamino)-4-nitrobenzene;
1-amino-2-tris(hydroxymethyl)methylamino-5-nitro-benzene;
1-hydroxy-2-amino-5-nitrobenzene;
1-hydroxy-2-amino-4-nitrobenzene;
1-hydroxy-3-nitro-4-aminobenzene;
1-hydroxy-2-amino-4,6-dinitrobenzene;
1-β-hydroxyethyloxy-2-β-hydroxyethylamino-5-nitro-benzene;
1-methoxy-2-β-hydroxyethylamino-5-nitrobenzene;

1-β-hydroxyethyloxy-3-methylamino-4-nitrobenzene;

1-βγ-dihydroxypropyloxy-3-methylamino-4-nitrobenzene;

1-β-hydroxyethylamino-4-β,γ-dihydroxypropyloxy-2-nitrobenzene;

1-β,γ-dihydroxypropylamino-4-trifluoromethyl-2-nitrobenzene;

1-β-hydroxyethylamino-4-trifluoromethyl-2-nitro-benzene;

1-β-hydroxyethylamino-3-methyl-2-nitrobenzene;

1-β-aminoethylamino-5-methoxy-2-nitrobenzene;

1-hydroxy-2-chloro-6-ethylamino-4-nitrobenzene;

1-hydroxy-2-chloro-6-amino-4-nitrobenzene;

1-hydroxy-6-bis(β-hydroxyethyl)amino-3-nitrobenzene;

1-β-hydroxyethylamino-2-nitrobenzene;

1-hydroxy-4-β-hydroxyethylamino-3-nitrobenzene.

Among the azo, azomethine, methine or tetraazapentamethine direct dyes that may be used according to the invention, mention may be made of the cationic dyes described in patent applications WO 95/15144, WO 95/01772 and EP 714 954; FR 2 189 006, FR 2 285 851, FR 2 140 205, EP 1 378 544 and EP 1 674 073.

Hence mention may be made especially of the following dyes of formulae (II) to (V), and preferably the compounds of formulae (II) and (IV):

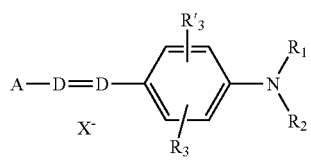
(II)

in which:

D represents a nitrogen atom or the —CH group, $R_1$ and $R_2$, which are identical or different, represent a hydrogen atom; a $C_1$-$C_4$ alkyl radical which may be substituted by a —CN, —OH or —NH$_2$ radical, or form, with a carbon atom of the benzene ring, an optionally oxygen-containing or nitrogen-containing heterocycle which may be substituted by one or more $C_1$-$C_4$ alkyl radicals; a 4'-aminophenyl radical, $R_3$ and $R'_3$, which are identical or different, represent a hydrogen or halogen atom selected from chlorine, bromine, iodine and fluorine, or a cyano, $C_1$-$C_4$ alkyl, $C_1$-$C_4$ alkoxy or acetyloxy radical, X⁻ represents an anion preferably selected from chloride, methyl sulphate and acetate, A represents a group selected from the following structures A1 to A18:

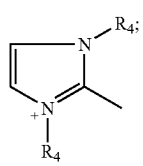 A₁

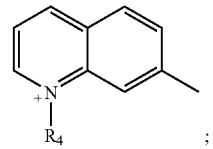 A₂

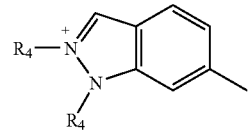 A₃

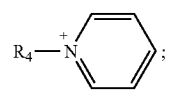 A₄

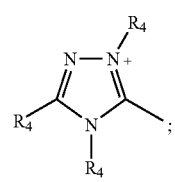 A₅

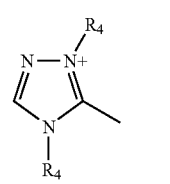 A₆

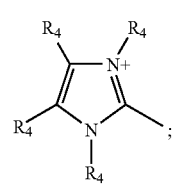 A₇

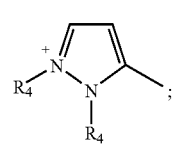 A₈

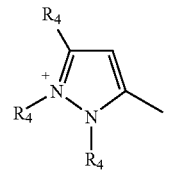 A₉

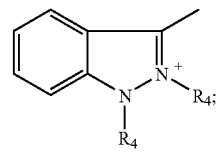 A₁₀

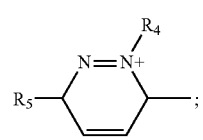 A₁₁

-continued

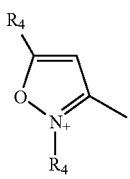 A12

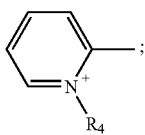 A13

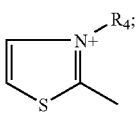 A14

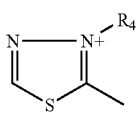 A15

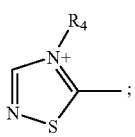 A16

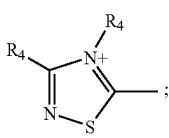 A17

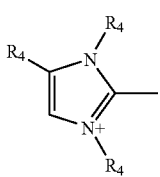 A18 in which $R_4$ represents a $C_1$-$C_4$ alkyl radical which may be substituted by a hydroxyl radical and $R_5$ represents a $C_1$-$C_4$ alkoxy radical

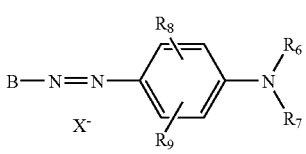 (III)

in which:
$R_6$ represents a hydrogen atom or a $C_1$-$C_4$ alkyl radical,
$R_7$ represents a hydrogen atom, an alkyl radical which may be substituted by a —CN radical or by an amino group, a 4'-aminophenyl radical, or, with $R_6$, forms a heterocycle which optionally contains oxygen and/or nitrogen and which may be substituted by a $C_1$-$C_4$ alkyl radical,
$R_8$ and $R_9$, which are identical or different, represent a hydrogen atom, a halogen atom such as bromine, chlorine, iodine or fluorine, a $C_1$-$C_4$ alkyl or $C_1$-$C_4$ alkoxy radical or a —CN radical, $X^-$ represents an anion preferably selected from chloride, methyl sulphate and acetate,
B represents a group selected from the structures B1 to B6 below:

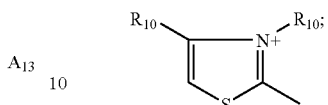 B1

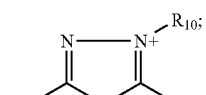 B2

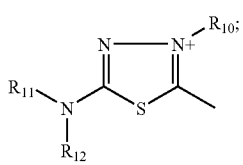 B3

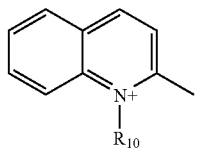 B4

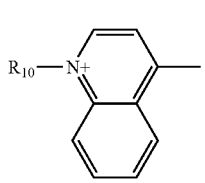 B5

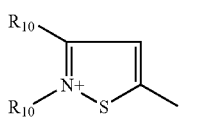 B6 in which $R_{10}$ represents a $C_1$-$C_4$ alkyl radical, and $R_{11}$ and $R_{12}$, which are identical or different, represent a hydrogen atom or a $C_1$-$C_4$ alkyl radical;

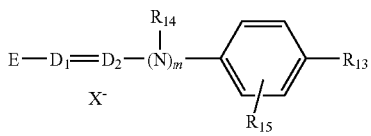 (IV)

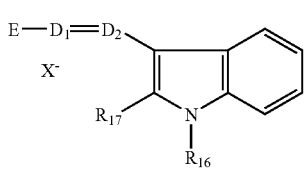 (IV')

in which:
$R_{13}$ represents a hydrogen atom, a $C_1$-$C_4$ alkoxy radical or a halogen atom such as bromine, chlorine, iodine or fluorine,
$R_{14}$ represents a hydrogen atom or a $C_1$-$C_4$ alkyl radical or, with a carbon atom of the benzene ring, forms a heterocycle which optionally contains oxygen and/or is substituted by one or more $C_1$-$C_4$ alkyl groups, $R_{15}$ represents a hydrogen atom or halogen atom such as bromine, chlorine, iodine or fluorine, $R_{16}$ and $R_{17}$, which are identical or different, represent a hydrogen atom or a $C_1$-$C_4$ alkyl radical, $D_1$ and $D_2$, which are identical or different, represent a nitrogen atom or the —CH group, m=0 or 1, with the proviso that, when $R_{13}$ represents an unsubstituted amino group, $D_1$ and $D_2$ then represent simultaneously a —CH group and m=0, $X^-$ represents an anion preferably selected from chloride, methyl sulphate and acetate, E represents a group selected from structures E1 to E8 below:

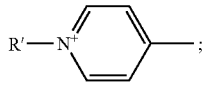
E1

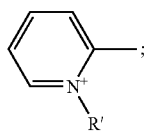
E2

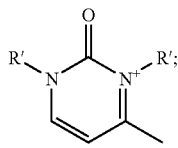
E3

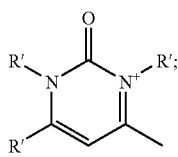
E4

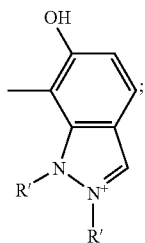
E5

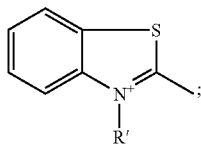
E6

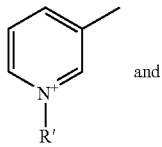
E7 and

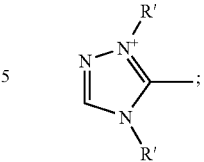
E8 in which R' represents a $C_1$-$C_4$ alkyl radical;

when m=0 and when $D_1$ represents a nitrogen atom, E may also denote a group of structure E9 below:

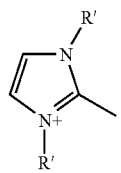
E9 in which R' represents a $C_1$-$C_4$ alkyl radical.

$$G-N=N-J \quad (V)$$

in which:

the symbol G represents a group selected from the structures $G_1$ to $G_3$ below:

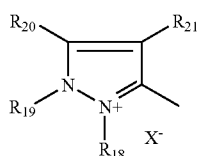
$G_1$

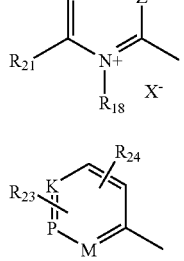
$G_2$ $G_3$ in which structures $G_1$ to $G_3$:

$R_{18}$ denotes a $C_1$-$C_4$ alkyl radical, a phenyl radical which may be substituted by a $C_1$-$C_4$ alkyl radical or a halogen atom selected from chlorine, bromine, iodine and fluorine;

$R_{19}$ denotes a $C_1$-$C_4$ alkyl radical or a phenyl radical;

$R_{20}$ and $R_{21}$, which are identical or different, represent a $C_1$-$C_4$ alkyl radical, a phenyl radical or together form in $G_1$ a benzene ring which is substituted by one or more $C_1$-$C_4$ alkyl, $C_1$-$C_4$ alkoxy or $NO_2$ radicals, or form together in $G_2$ a benzene ring which is optionally substituted by one or more $C_1$-$C_4$ alkyl, $C_1$-$C_4$ alkoxy or $NO_2$ radicals;

$R_{20}$ may also denote a hydrogen atom;

Z denotes an oxygen or sulphur atom or a group —$NR_{19}$;

M represents a group —CH, —CR (R denoting $C_1$-$C_4$ alkyl) or —$NR_{22}$ $(X^-)_r$;

K represents a group —CH, —CR (R denoting $C_1$-$C_4$ alkyl) or —$NR_{22}$ ($X^-$)$_r$;

P represents a group —CH, —CR (R denoting $C_1$-$C_4$ alkyl) or —$NR_{22}$ ($X^-$)$_r$; r denotes zero or 1;

$R_{22}$ represents an $O^-$ atom, a $C_1$-$C_4$ alkoxy radical or a $C_1$-$C_4$ alkyl radical;

$R_{23}$ and $R_{24}$, which are identical or different, represent a hydrogen or halogen atom selected from chlorine, bromine, iodine and fluorine, or a $C_1$-$C_4$ alkyl or $C_1$-$C_4$ alkoxy radical, or an —$NO_2$ radical;

$X^-$ represents an anion preferably selected from chloride, iodide, methyl sulphate, ethyl sulphate, acetate and perchlorate;

with the provisos that if $R_{22}$ denotes $O^-$, r denotes zero;

if K or P or M denote —N—$C_1$-$C_4$ alkyl $X^-$, $R_{23}$ or $R_{24}$ is or is not different from a hydrogen atom;

if K denotes —$NR_{22}$ ($X^-$)$_r$, M=P=—CH, —CR;

if M denotes —$NR_{22}$($X^-$)$_r$, K=P=—CH, —CR;

if P denotes —$NR_{22}$($X^-$)$_r$, K=M and they denote —CH or —CR;

if Z denotes a sulphur atom with $R_{21}$ denoting $C_1$-$C_4$ alkyl, $R_{20}$ is different from a hydrogen atom;

if Z denotes —$NR_{22}$ with $R_{19}$ denoting $C_1$-$C_4$ alkyl, at least one of the radicals, $R_{18}$, $R_{20}$ or $R_{21}$, of the group with structure $G_2$ is different from a $C_1$-$C_4$ alkyl radical;

the symbol J represents:

(a) a group of structure $J_1$ below:

in which structure $J_1$ $R_{25}$ represents a hydrogen atom, a halogen atom selected from chlorine, bromine, iodine and fluorine, a $C_1$-$C_4$ alkyl or $C_1$-$C_4$ alkoxy radical, a radical —OH, —$NO_2$, —$NHR_{28}$, —$NR_{29}R_{30}$, —NHCO—$C_1$-$C_4$ alkyl, or with $R_{26}$, forms a 5- or 6-membered ring containing or not containing one or more heteroatoms selected from nitrogen, oxygen or sulphur;

$R_{26}$ represents a hydrogen atom, a halogen atom selected from chlorine, bromine, iodine and fluorine, or a $C_1$-$C_4$ alkyl or $C_1$-$C_4$ alkoxy radical, or, with $R_{27}$ or $R_{28}$, forms a 5- or 6-membered ring containing or not containing one or more heteroatoms selected from nitrogen, oxygen or sulphur;

$R_{27}$ represents a hydrogen atom, an —OH radical, a radical —$NHR_{28}$ or a radical —$NR_{29}R_{30}$;

$R_{28}$ represents a hydrogen atom, a $C_1$-$C_4$ alkyl radical, a $C_1$-$C_4$ monohydroxyalkyl or $C_2$-$C_4$ polyhydroxyalkyl radical or a phenyl radical;

$R_{29}$ and $R_{30}$, which are identical or different, represent a $C_1$-$C_4$ alkyl radical or a $C_1$-$C_4$ monohydroxyalkyl or $C_2$-$C_4$ polyhydroxyalkyl radical;

(b) a 5- or 6-membered, nitrogen-containing heterocyclic group which may contain other heteroatoms and/or carbonyl groups and may be substituted by one or more $C_1$-$C_4$ alkyl, amino or phenyl radicals, and especially a group of structure $J_2$ below:

in which structure $J_2$ $R_{31}$ and $R_{32}$, which are identical or different, represent a hydrogen atom, a $C_1$-$C_4$ alkyl radical or phenyl radical;

Y denotes the radical —CO— or the radical $$-\overset{CH_3}{\underset{}{C}}=;$$

n=0 or 1, and, when n denotes 1, U denotes the —CO— radical.

In the above-defined structures (II) to (V), the $C_1$-$C_4$ alkyl or alkoxy group preferably denotes methyl, ethyl, butyl, methoxy or ethoxy.

Among the compounds of formulae (II) and (IV), preference is given to the following compounds:

We may also mention, among the azo direct dyes, the following dyes described in the COLOUR INDEX INTERNATIONAL 3rd edition:

Disperse Red 17
Basic Red 22
Basic Red 76
Basic Yellow 57
Basic Brown 16
Basic Brown 17
Disperse Black 9.

We may also mention 1-(4'-aminodiphenylazo)-2-methyl-4-bis(β-hydroxyethyl)aminobenzene.

Among the quinone direct dyes, we may mention the following dyes:
Disperse Red 15
Solvent Violet 13
Disperse Violet 1
Disperse Violet 4
Disperse Blue 1
Disperse Violet 8
Disperse Blue 3
Disperse Red 11
Disperse Blue 7
Basic Blue 22
Disperse Violet 15
Basic Blue 99 as well as the following compounds:
1-N-methylmorpholiniumpropylamino-4-hydroxyanthraquinone
1-aminopropylamino-4-methylaminoanthraquinone
1-aminopropylaminoanthraquinone
5-β-hydroxyethyl-1,4-diaminoanthraquinone
2-aminoethylaminoanthraquinone
1,4-bis(β,γ-dihydroxypropylamino)anthraquinone.

Among the azine dyes, we may mention the following compounds:
Basic Blue 17
Basic Red 2.

Among the triarylmethane dyes usable according to the invention, we may mention the following compounds:
Basic Green 1
Basic Violet 3
Basic Violet 14
Basic Blue 7
Basic Blue 26

Among the indoamine dyes that may be used according to the invention, mention may be made of the following compounds:
2-β-hydroxyethylamino-5-[bis(β-4'-hydroxyethyl)-amino]anilino-1,4-benzoquinone
2-β-hydroxyethylamino-5-(2'-methoxy-4'-amino)anilino-1,4-benzoquinone
3-N-(2'-chloro-4'-hydroxy)phenylacetylamino-6-methoxy-1,4-benzoquinone imine
3-N-(3'-chloro-4'-methylamino)phenylureido-6-methyl-1,4-benzoquinone imine
3-[4'-N-(ethyl,carbamylmethyl)amino]phenylureido-6-methyl-1,4-benzoquinone imine.

Among the dyes of tetraazapentamethine type that may be used according to the invention, mention may be made of the following compounds given in the table below, An being defined as previously:

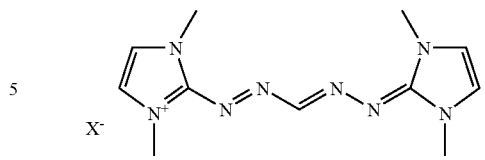

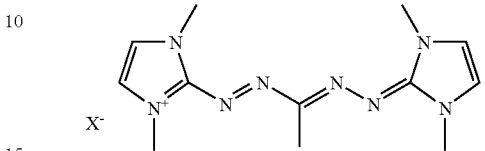

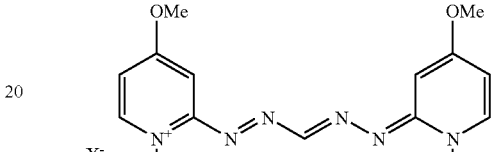

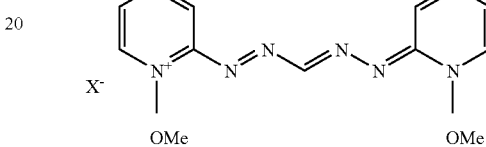

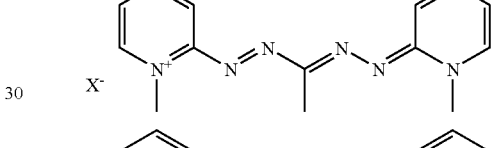

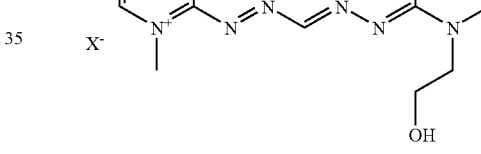

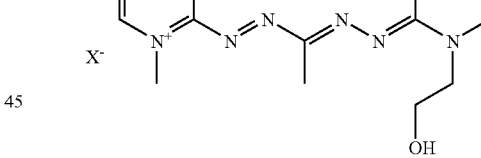

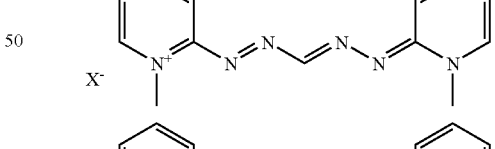

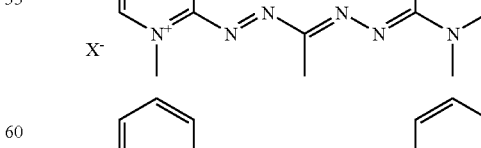

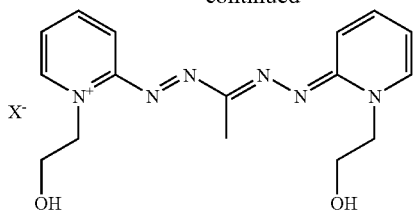

X⁻ represents an anion preferably selected from chloride, iodide, methyl sulphate, ethyl sulphate, acetate and perchlorate.

Among the polychromophoric dyes, mention may be made more particularly of symmetrical or nonsymmetrical azo and/or azomethine (hydrazone) di- or trichromophoric dyes comprising, on the one hand, at least one optionally fused 5- or 6-membered aromatic heterocycle, comprising at least one quaternized nitrogen atom engaged in said heterocycle and optionally at least one other heteroatom (such as nitrogen, sulphur or oxygen), and, on the other hand, at least one optionally substituted phenyl or naphthyl group, optionally bearing at least one group OR with R representing a hydrogen atom, an optionally substituted $C_1$-$C_6$ alkyl radical, an optionally substituted phenyl nucleus, or at least one group $N(R')_2$ with R', which may be identical or different, representing a hydrogen atom, an optionally substituted $C_1$-$C_6$ alkyl radical or an optionally substituted phenyl nucleus; the radicals R' possibly forming, with the nitrogen atom to which they are attached, a saturated 5- or 6-membered heterocycle, or alternatively one and/or both the radicals R' may each form, with the carbon atom of the aromatic ring located ortho to the nitrogen atom, a saturated 5- or 6-membered heterocycle.

Aromatic cationic heterocycles that may preferably be mentioned include 5- or 6-membered rings containing 1 to 3 nitrogen atoms and preferably 1 or 2 nitrogen atoms, one being quaternized, and said heterocycle moreover being optionally fused to a benzene nucleus. It should similarly be noted that the heterocycle may optionally comprise another heteroatom other than nitrogen, for instance sulphur or oxygen.

If the heterocycles or phenyl or naphthyl groups are substituted, they are substituted, for example, by one or more $C_1$-$C_8$ alkyl radicals optionally substituted by a hydroxyl, $C_1$-$C_2$ alkoxy, $C_2$-$C_4$ hydroxyalkoxy, acetylamino or amino group substituted by one or two $C_1$-$C_4$ alkyl radicals optionally bearing at least one hydroxyl group, or the two radicals possibly forming, with the nitrogen atom to which they are attached, a 5- or 6-membered heterocycle, optionally comprising another heteroatom identical to or different than nitrogen; a halogen atom; a hydroxyl group; a $C_1$-$C_2$ alkoxy radical; a $C_2$-$C_4$ hydroxyalkoxy radical; an amino radical; an amino radical substituted by one or two identical or different $C_1$-$C_4$ alkyl radicals, optionally bearing at least one hydroxyl group.

These polychromophores are connected together by means of at least one linker optionally comprising at least one quaternized nitrogen atom that may or may not be part of a saturated or unsaturated, optionally aromatic heterocycle.

Preferably, the linker is a linear, branched or cyclic $C_1$-$C_{20}$ alkyl chain, optionally interrupted by at least one heteroatom (such as nitrogen or oxygen) and/or by at least one group comprising such a heteroatom (CO or $SO_2$), optionally interrupted by at least one heterocycle that may or may not be fused to a phenyl nucleus and comprising at least one quaternized nitrogen atom that is part of said ring and optionally at least one other heteroatom (such as oxygen, nitrogen or sulphur), optionally interrupted by at least one substituted or unsubstituted phenyl or naphthyl group, optionally at least one quaternary ammonium group substituted by two optionally substituted $C_1$-$C_{15}$ alkyl groups, the linker not comprising any nitro, nitroso or peroxy groups.

The bonding between the linker and each chromophore generally takes place via a heteroatom substituent on the phenyl or naphthyl nucleus or via the quaternized nitrogen atom of the cationic heterocycle.

The dye may comprise identical or different chromophores.

As examples of such dyes, reference may be made especially to patent applications EP 1 637 566, EP 1 619 221, EP 1 634 926, EP 1 619 220, EP 1 672 033, EP 1 671 954, EP 1 671 955, EP 1 679 312, EP 1 671 951, EP 167 952, EP 167 971, WO 06/063 866, WO 06/063 867, WO 06/063 868, WO 06/063 869, EP 1 408 919, EP 1 377 264, EP 1 377 262, EP 1 377 261, EP 1 377 263, EP 1 399 425, EP 1 399 117, EP 1 416 909, EP 1 399 116 and EP 1 671 560.

It is also possible to use the cationic direct dyes mentioned in patent applications: EP 1 006 153, which describes dyes comprising two chromophores of anthraquinone type connected via a linker of cationic type; EP 1 433 472, EP 1 433 474, EP 1 433 471 and EP 1 433 473, which describe identical or different dichromophoric dyes, connected via a cationic or noncationic linker, and also EP 6 291 333, which especially describes dyes comprising three chromophores, one of them being an anthraquinone chromophore, to which are attached two chromophores of azo or diazacarbocyanine type or an isomer thereof.

Among the natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin, and apigenidin. It is also possible to use extracts or decoctions containing these natural dyes and especially henna-based poultices or extracts.

The direct dye(s) more particularly represent(s) from 0.0001% to 10% by weight, relative to the total weight of the composition, and preferably from 0.005% to 5% by weight, relative to the total weight of the composition.

The direct dyes employed are preferably neutral or cationic direct dyes.

In accordance with one particular embodiment of the invention, the composition comprising the amino silicon compound or compounds of formula (I) comprises one or more fatty substances.

The term "fatty substance" means an organic compound that is insoluble in water at ordinary temperature (25° C.) and at atmospheric pressure (760 mmHg) (solubility of less than 5%, preferably than 1% and even more preferentially than 0.1%). Moreover, these organic compounds preferably possess lubricant properties. In particular, for the purposes of the present invention, a fatty substance is a compound selected from a fatty alcohol, fatty acid, fatty acid ester, fatty alcohol ester, mineral, vegetable, animal or synthetic oil, silicone or wax. It is recalled that, for the purposes of the invention, the fatty alcohols, fatty esters and fatty acids contain at least one linear or branched, saturated or unsaturated hydrocarbon group containing 6 to 30 carbon atoms, which is optionally substituted, in particular by one or more hydroxyl groups (in particular 1 to 4). If they are unsaturated, these compounds may comprise one to three conjugated or non-conjugated carbon-carbon double bonds.

As oils that may be used in the composition of the invention, examples that may be mentioned include:

hydrocarbon oils of animal origin, such as perhydrosqualene;

hydrocarbon oils of plant origin, such as liquid fatty acid triglycerides containing from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by the company Stéarineries Dubois or those sold under the names Miglyol® 810, 812 and 818 by the company Dynamit Nobel, jojoba oil and shea butter oil;

linear or branched hydrocarbons of mineral or synthetic origin, of more than 16 carbon atoms, such as volatile or non-volatile liquid paraffins, and derivatives thereof, petroleum jelly, liquid petroleum jelly, polydecenes, and hydrogenated polyisobutene such as Parleam®; and isoparaffins, for instance isohexadecane and isodecane.

fatty alcohols are saturated or unsaturated, linear or branched, and contain from 8 to 30 carbon atoms: mention may be made of cetyl alcohol, stearyl alcohol and a mixture thereof (cetylstearyl alcohol), octyldodecanol, 2-butyloctanol, 2-hexyldecanol, 2-undecylpentadecanol, oleyl alcohol or linoleyl alcohol;

partially hydrocarbon- and/or silicone-based fluoro oils, for instance those described in document JP-A-2-295912; fluoro oils also include perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name Foralkyl® by the company Atochem; nonafluoromethoxy-butane and nonafluoroethoxyisobutane; perfluoromorpho-line derivatives, such as 4-trifluoromethyl perfluoromorpho-line sold under the name PF 5052® by the company 3M.

The wax or waxes are selected particularly from carnauba wax, candelilla wax, esparto grass wax, paraffin wax, ozokerites, plant waxes such as olive wax, rice wax, hydrogenated jojoba wax or the absolute waxes of flowers such as the essential wax of blackcurrant blossom sold by the company Bertin (France), animal waxes, for instance beeswaxes or modified beeswaxes (cerabellina); other waxes or waxy starting materials that may be used according to the invention are especially marine waxes such as the product sold by the company Sophim under the reference M82, and polyethylene waxes or polyolefin waxes in general.

The fatty acids that may be used in the composition of the invention may be saturated or unsaturated and contain from 6 to 30 carbon atoms and in particular from 9 to 30 carbon atoms. They are more particularly selected from myristic acid, palmitic acid, stearic acid, behenic acid, oleic acid, linoleic acid, linolenic acid and isostearic acid.

The esters are esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total carbon number of the esters being greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, 2-hexyldecyl laurate.

Still in the context of this variant, esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxy alcohols may also be used.

The following may especially be mentioned: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetrasononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

Among the esters mentioned above, it is preferred to use ethyl, isopropyl, myristyl, cetyl or stearyl palmitate, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isononyl isononanoate or cetyl octanoate.

The composition may also comprise, as fatty ester, sugar esters and diesters of $C_6$-$C_{30}$ and preferably $C_{12}$-$C_{22}$ fatty acids. It is recalled that the term "sugar" means oxygen-bearing hydrocarbon compounds containing a plurality of alcohol functions, with or without aldehyde or ketone functions, and comprising at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, especially alkyl derivatives, such as methyl derivatives, for instance methylglucose.

The sugar esters of fatty acids may be selected especially from the group containing the esters or mixtures of esters of sugars described previously and of linear or branched, saturated or unsaturated $C_6$-$C_{30}$ and preferably $C_{12}$-$C_{22}$ fatty acids. If they are unsaturated, these compounds may comprise one to three conjugated or nonconjugated carbon-carbon double bonds.

The esters according to this variant may also be selected from mono-, di-, tri-, tetraesters and polyesters, and mixtures thereof.

These esters may be, for example, oleates, laurates, palmitates, myristates, behenates, cocoates, stearates, linoleates, linolenates, caprates and arachidonates, or mixtures thereof such as, especially, oleo-palmitate, oleo-stearate and palmito-stearate mixed esters.

Use is made more particularly of monoesters and diesters and especially sucrose, glucose or methyl-glucose mono- or dioleates, stearates, behenates, oleopalmitates, linoleates, linolenates and oleo-stearates.

An example that may be mentioned is the product sold under the name Glucate® DO by the company Amerchol, which is a methylglucose dioleate.

Examples of esters or mixtures of esters of sugar and of fatty acid that may also be mentioned include:
- the products sold under the names F160, F140, F110, F90, F70 and SL40 by the company Crodesta, respectively denoting sucrose palmitostearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;
- the products sold under the name Ryoto Sugar Esters, for example referenced B370 and corresponding to sucrose behenate formed from 20% monoester and 80% di-tri-ester-polyester;
- the sucrose mono-dipalmito-stearate sold by the company Goldschmidt under the name Tegosoft® PSE.

The silicones that may be used in the cosmetic compositions of the present invention are volatile or non-volatile, cyclic, linear or branched silicones, which are unmodified or modified with organic groups, having a viscosity from $5\times10^{-6}$ to 2.5 m$^2$/s at 25° C., and preferably $1\times10^{-5}$ to 1 m$^2$/s.

The silicones that may be used in accordance with the invention may take the form of oils, waxes, resins or gums.

Preferably, the silicone is selected from polydialkylsiloxanes, especially polydimethylsiloxanes (PDMS), and organomodified polysiloxanes comprising at least one functional group selected from poly(oxy-alkylene) groups, amino groups and alkoxy groups.

Organopolysiloxanes are defined in greater detail in Walter Noll's "Chemistry and Technology of Silicones" (1968) Academic Press. They may be volatile or non-volatile.

When they are volatile, the silicones are more particularly selected from those having a boiling point of between 60° C. and 260° C., and even more particularly from:

(i) cyclic polydialkylsiloxanes containing from 3 to 7 and preferably 4 to 5 silicon atoms. These are, for example, octamethylcyclotetrasiloxane sold in particular under the name Volatile Silicone® 7207 by Union Carbide or Silbione® 70045 V 2 by Rhodia, decamethylcyclopentasiloxane sold under the name Volatile Silicone® 7158 by Union Carbide, and Silbione® 70045 V 5 by Rhodia, and mixtures thereof.

Mention may also be made of cyclocopolymers of the dimethylsiloxane/methylalkylsiloxane type, such as Volatile Silicone® FZ 3109 sold by the company Union Carbide, of formula:

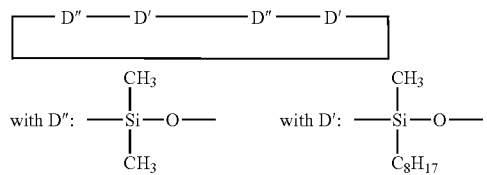

Mention may also be made of mixtures of cyclic polydialkylsiloxanes with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane;

(ii) linear volatile polydialkylsiloxanes containing 2 to 9 silicon atoms and having a viscosity of less than or equal to $5\times10^{-6}$ m$^2$/s at 25° C. An example is decamethyltetrasiloxane sold in particular under the name SH 200 by the company Toray Silicone. Silicones belonging to this category are also described in the article published in Cosmetics and Toiletries, Vol. 91, Jan. 76, pp. 27-32, Todd & Byers "Volatile Silicone Fluids for Cosmetics".

Non-volatile polydialkylsiloxanes, polydialkyl-siloxane gums and resins, polyorganosiloxanes modified with organofunctional groups above, and mixtures thereof, are preferably used.

These silicones are more particularly selected from polydialkylsiloxanes, among which mention may be made mainly of polydimethylsiloxanes containing trimethyl-silyl end groups. The viscosity of the silicones is measured, for example, at 25° C. according to ASTM standard 445 Appendix C.

Among these polydialkylsiloxanes, mention may be made, in a non-limiting manner, of the following commercial products:
- the Silbione® oils of the 47 and 70 047 series or the Mirasil® oils sold by Rhodia, for instance the oil 70 047 V 500 000;
- the oils of the Mirasil®, series sold by the company Rhodia;
- the oils of the 200 series from the company Dow Corning, such as DC200 with a viscosity of 60 000 mm$^2$/s;
- the Viscasil® oils from General Electric and certain oils of the SF series (SF 96, SF 18) from General Electric.

Mention may also be made of polydimethylsiloxanes containing dimethylsilanol end groups known under the name Dimethiconol (CTFA), such as the oils of the 48 series from the company Rhodia.

In this category of polydialkylsiloxanes, mention may also be made of the products sold under the names Abil Wax® 9800 and 9801 by the company Goldschmidt, which are poly ($C_1$-$C_{20}$)dialkylsiloxanes.

The silicone gums that can be used in accordance with the invention are especially polydialkylsiloxanes and preferably polydimethylsiloxanes with high number-average molecular masses of between 200 000 and 1 000 000, used alone or as a mixture in a solvent. This solvent can be chosen from volatile silicones, polydimethylsiloxane (PDMS) oils, polyphenyl-methylsiloxane (PPMS) oils, isoparaffins, polyiso-butylenes, methylene chloride, pentane, dodecane and tridecane, or mixtures thereof.

Products that can be used more particularly in accordance with the invention are mixtures such as:
- mixtures formed from a polydimethylsiloxane hydroxylated at the chain end, or dimethiconol (CTFA) and from a cyclic polydimethylsiloxane also known as cyclomethicone (CTFA), such as the product Q2 1401 sold by the company Dow Corning;
- mixtures formed from a polydimethylsiloxane gum with a cyclic silicone, such as the product SF 1214 Silicone Fluid from the company General Electric; this product is an SF 30 gum corresponding to a dimethicone, having a number-average molecular weight of 500 000, dissolved in the oil SF 1202 Silicone Fluid corresponding to decamethylcyclopentasiloxane;
- mixtures of two PDMSs with different viscosities, and more particularly of a PDMS gum and a PDMS oil, such as the product SF 1236 from the company General Electric. The product SF 1236 is a mixture of an SE 30 gum defined above, having a viscosity of 20 m$^2$/s, and an SF 96 oil, with a viscosity of $5 \times 10^{-6}$ m$^2$/s. This product preferably contains 15% SE 30 gum and 85% SF 96 oil.

The organopolysiloxane resins that can be used in accordance with the invention are crosslinked siloxane systems containing the following units:

$R_2SiO_{2/2}$, $R_3SiO_{1/2}$, $RsiO_{3/2}$ and $SiO_{4/2}$ in which R represents an alkyl possessing 1 to 16 carbon atoms. Among these products, the ones that are particularly preferred are those in which R denotes a $C_1$-$C_4$ lower alkyl group, more particularly methyl.

Among these resins, mention may be made of the product sold under the name Dow Corning 593 or those sold under the names Silicone Fluid SS 4230 and SS 4267 by the company General Electric, which are silicones of dimethyl/trimethyl siloxane structure.

Mention may also be made of trimethyl siloxy-silicate type resins sold in particular under the names X22-4914, X21-5034 and X21-5037 by the company Shin-Etsu.

The organomodified silicones that can be used in accordance with the invention are silicones as defined above and comprising in their structure one or more organofunctional groups attached via a hydrocarbon group.

Besides the silicones described above, the organomodified silicones may be polydiarylsiloxanes, especially polydiphenylsiloxanes, and polyalkylaryl-siloxanes functionalized with the organofunctional groups mentioned previously.

The polyalkylarylsiloxanes are selected particularly from linear and/or branched polydimethyl/methylphenylsiloxanes and polydimethyl/di-phenylsiloxanes with a viscosity of from $1 \times 10^{-5}$ to $5 \times 10^{-2}$ m$^2$/s at 25° C.

Among these polyalkylarylsiloxanes, examples that may be mentioned include the products sold under the following names:

the Silbione® oils of the 70 641 series from Rhodia;
the oils of the Rhodorsil® 70 633 and 763 series from Rhodia;
the oil Dow Corning 556 Cosmetic Grade Fluid from Dow Corning;
the silicones of the PK series from Bayer, such as the product PK20;
the silicones of the PN and PH series from Bayer, such as the products PN1000 and PH1000;
certain oils of the SF series from General Electric, such as SF 1023, SF 1154, SF 1250 and SF 1265.

Among the organomodified silicones, mention may be made of polyorganosiloxanes comprising:

polyethyleneoxy and/or polypropyleneoxy groups optionally comprising $C_6$-$C_{24}$ alkyl groups, such as the products known as dimethicone copolyol sold by the company Dow Corning under the name DC 1248 or the oils Silwet® L 722, L 7500, L 77 and L 711 by the company Union Carbide, and the ($C_{12}$)alkylmethicone copolyol sold by the company Dow Corning under the name Q2 5200;
substituted or unsubstituted amine groups, such as the products sold under the name GP 4 Silicone Fluid and GP 7100 by the company Genesee, or the products sold under the names Q2 8220 and Dow Corning 929 or 939 by the company Dow Corning. The substituted amine groups are, in particular, $C_1$-$C_4$ aminoalkyl groups;
alkoxylated groups such as the product sold under the name Silicone Copolymer F-755 by SWS Silicones, and Abil Wax® 2428, 2434 and 2440 by the company Goldschmidt.

Preferably, the fatty substance is a compound that is liquid at a temperature of 25° C. and at atmospheric pressure.

It is preferably a fatty acid ester or liquid petrolatum.

The composition comprising the amino silicon compound or compounds according to the invention has a fatty substance content of advantageously between 10% and 99% by weight, relative to the weight of the composition, preferably between 20% and 90% by weight, preferentially between 25% and 80% and more preferably between 30% and 70% by weight.

According to one particular embodiment of the invention, this composition comprises one or more surfactants; these surfactants may be nonionic, anionic, cationic or amphoteric.

The composition preferably comprises one or more anionic surfactants, more especially selected from the salts (in particular alkali metal salts, especially sodium salts, ammonium salts, amine salts, amino alcohol salts or alkaline-earth metal salts such as magnesium salts) of the following compounds:

alkyl sulphates, alkyl ether sulphates, alkylamido ether sulphates, alkylaryl polyether sulphates, monoglyceride sulphates;
alkylsulphonates, alkylamidesulphonates, alkylarylsulphonates, α-olefinsulphonates, paraffin-sulphonates;
alkyl phosphates, alkyl ether phosphates;
alkylsulphosuccinates, alkyl ether sulphosuccinates, alkylamidesulphosuccinates; alkyl-sulphosuccinamates;
alkylsulphoacetates;
acylsarcosinates; acylisethionates and N-acyl-taurates;
salts of fatty acids such as oleic acid, ricinoleic acid, palmitic acid or stearic acid, coconut oil acid or hydrogenated coconut oil acid;
alkyl-D-galactoside uronic acid salts;
acyllactylates;
salts of polyoxyalkylenated alkyl ether carboxylic acids, of polyoxyalkylenated alkylaryl ether carboxylic acids or of polyoxyalkylenated alkylamido ether carboxylic acids, in particular those containing from 2 to 50 ethylene oxide groups;
and mixtures thereof.

It should be noted that the alkyl or acyl radical of these various compounds advantageously contains from 6 to 24 carbon atoms, and preferably from 8 to 24 carbon atoms, and the aryl radical preferably denotes a phenyl or benzyl group.

The surfactant or mixture of surfactants, when present, represent(s) more particularly from 0.01% to 60% by weight, relative to the weight of the composition, preferably between 0.5% and 50% by weight and more preferably still between 1% and 40% by weight, very preferably between 4% and 30% by weight.

The composition comprising the amino silicon compound or compounds of formula (I) may further comprise an alkalifying agent different from said amino silicon compound or compounds.

Alkalifying agents include, for example, alone or in mixtures, aqueous ammonia; compounds of the following formula:

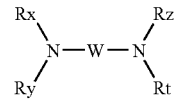

in which W is a propylene residue which is optionally substituted by a hydroxyl group or a $C_1$-$C_6$ alkyl radical, and Rx, Ry, Rz and Rt, which are identical or different, represent a hydrogen atom or a $C_1$-$C_6$ alkyl or $C_1$-$C_6$ hydroxyalkyl radical.

The additional alkalifying agent, if present, is preferably not aqueous ammonia. This agent allows the pH of the composition applied to hair, or at least its aqueous part, if present, to be regulated. This pH is preferably between 4 and 11 and more preferably between and 10.5. If aqueous ammonia is employed as an additional alkalifying agent, then its amount is preferably less than or equal to 0.03% by weight of the final composition (expressed as $NH_3$), more particularly less than or equal to 0.01% by weight, relative to the final composition. It is recalled that the final composition results from the mixing of the composition containing the compound or compounds of formula (I) with the oxidizing composition, this mixing being carried out either before application to the keratin fibres (extemporaneous preparation) or directly to the keratin fibres (successive separate application, without intermediate rinsing, of the compositions to the keratin fibres). Aqueous ammonia is preferably not employed as an additional alkalifying agent.

The composition comprising the aminosilicon compound(s) of formula (I) may also contain various adjuvants conventionally used in compositions for colouring the hair, such as anionic, cationic, nonionic, amphoteric or zwitterionic polymers or mixtures thereof; mineral thickeners, and in particular fillers such as clays or talc; organic thickeners, in particular with anionic, cationic, nonionic and amphoteric polymeric associative thickeners; antioxidants; penetrants; sequestrants; fragrances; dispersants; film-forming agents; ceramides; preservatives; opacifiers.

The adjuvants above are generally present in an amount, for each of them, of between 0.01% and 20% by weight relative to the weight of the composition.

The composition according to the invention may result from the extemporaneous mixing of the amino silicon compound or compounds of the invention with the remainder of the composition, containing less than 10% of water.

The colouring method according to the invention is implemented by applying the composition as defined above to the wet or dry keratin fibres, or by mixing said composition, extemporaneously or on the hair, with an aqueous composition.

According to the method in accordance with the invention, the composition is contacted with a composition comprising one or more oxidizing agents (oxidizing composition).

More particularly, the oxidizing composition is aqueous and optionally comprises one or more organic solvents.

Organic solvents include, for example, linear or branched $C_2$-$C_4$ alkanols, such as ethanol and isopropanol; glycerol; glycols and glycol ethers, for instance 2-butoxyethanol, propylene glycol, dipropylene glycol, propylene glycol monomethyl ether, diethylene glycol monoethyl ether and monomethyl ether, and also aromatic alcohols such as benzyl alcohol or phenoxyethanol, and mixtures thereof.

The solvent or solvents may be present in proportions of typically from 1% to 40% by weight relative to the weight of the oxidizing composition, and preferably from 5% to 30% by weight.

The oxidizing agent is selected more particularly from hydrogen peroxide; urea peroxide; alkali metal ferricyanides or bromides; peroxygenated salts such as, for example, persulphates, perborates and percarbonates of alkali metals or alkaline earth metals, such as sodium, potassium and magnesium; or mixtures thereof.

This oxidizing agent is advantageously composed of hydrogen peroxide, and more particularly by an aqueous solution whose titre may vary, more particularly, from 1 to 40 volumes, and more preferably still from 5 to 40 volumes.

The oxidizing composition may also comprise at least one alkalifying agent and/or at least one acidifying agent. The oxidizing composition preferably comprises at least one acidifying agent.

Acidifying agents include, for example, organic or inorganic acids, such as hydrochloric acid, orthophosphoric acid, sulphuric acid, carboxylic acids such as acetic acid, tartaric acid, citric acid and lactic acid, and sulphonic acids.

The pH of the oxidizing composition is usually less than 7.

The oxidizing composition may take the form of a solution, an emulsion or a gel.

The oxidizing composition may also include other ingredients conventionally used in the field, in particular those detailed above within the context of the composition comprising the aminosilicon compound(s) of formula (I).

According to one particular embodiment of the invention, the amount of oxidizing composition relative to that of the composition comprising the organosilicon compound or compounds is such that the amount of organosilicon compound of formula (I) is between 2% and 8% by weight in the final composition. Final composition is the term, it is recalled, defining the composition resulting from the mixing of the composition comprising the compound or compounds of formula (I) with the oxidizing composition, this mixing being carried out either before application to the keratin fibres (extemporaneous preparation) or directly on the keratin fibres (separate, successive application, without intermediate rinsing, of the compositions to the keratin fibres).

According to a first embodiment of the invention, the method is implemented by applying to the wet or dry keratin fibres a composition obtained by extemporaneous mixing, at the time of use, of the composition comprising the amino silicon compound or compounds of formula (I) (first composition) and the oxidizing composition (second composition).

According to a second embodiment of the invention, the method is implemented by applying both compositions to the wet or dry keratin fibres in succession and without intermediate rinsing.

More particularly, the method is implemented by applying to the wet or dry keratin fibres, in succession and without intermediate rinsing, in particular with water, the composition comprising the amino silicon compound or compounds of formula (I) (first composition) and then the oxidizing composition (second composition).

According to another possibility, the method is implemented by applying to the wet or dry keratin fibres, in succession and without intermediate rinsing, in particular with water, the oxidizing composition (second composition) and then the composition comprising the amino silicon compound or compounds of formula (I) (first composition).

Irrespective of the version of the method that is employed, the mixture present on the fibres (resulting either from the extemporaneous mixing or from the successive application of the composition comprising one or more amino silicon compounds of formula (I) and of the oxidizing composition) is left in place for a duration, in general, of the order of 1 minute to 1 hour, preferably of 10 minutes to 30 minutes.

The temperature during the method is conventionally between the ambient temperature (between 15 to 25° C.) and 80° C., preferably between ambient temperature and 60° C.

At the end of the treatment, the human keratin fibres are optionally rinsed with water, washed with shampoo, rinsed again with water, and then dried or left to dry.

The invention additionally provides a composition having a water content of less than 10% by weight, comprising one or more aminoalkoxysilanes of formula (I) detailed above, in combination with one or more fatty substances.

The composition preferably has a water content of less than or equal to 2% by weight, more advantageously less than 1% by weight.

The composition preferably does not comprise any bound water, such as the water of crystallization of the salts, or traces of water absorbed by the raw materials used in producing the compositions according to the invention.

Everything detailed beforehand concerning the composition comprising the amino silicon compound or compounds of formula (I) remains applicable and will therefore not be repeated in this section of the description.

The invention, lastly, provides a multiple-compartment device comprising in at least one of its compartments a composition comprising one or more amino silicon compound of formula (I) as defined above and in at least one other compartment a composition comprising one or more oxidizing agents, likewise described above.

The examples which follow serve to illustrate the invention, though without any limitative character.

EXAMPLE 1

Lightening Compositions

1. The Compositions According to the Invention (the Amounts are Expressed in g %)

|  | Composition 1 | Composition 2 |
|---|---|---|
| Sodium lauryl sulphate in powder form | 11.25 | 10 |
| Talc | 33.75 | 30 |
| Isopropyl myristate | 45 | 40 |
| (3-Aminopropyl)triethoxysilane (1) | 10 | 0 |
| (3-Aminopropyl)tris[2-(2-methoxy-ethoxy]silane (2) | 0 | 20 |

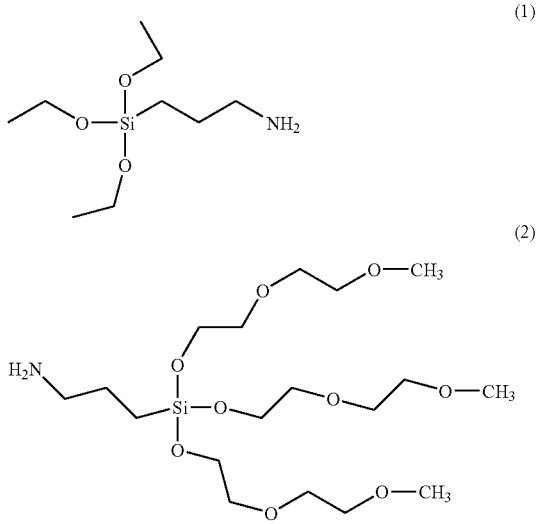

2. Non-Inventive Aqueous Composition Based on Aqueous Ammonia (the Amounts are Expressed in g %)

| Polyglycerolated oleyl alcohol with 2 mol of glycerol | 4 |
|---|---|
| Polyglycerolated oleyl alcohol with 4 mol of glycerol | 5.69 AI (*) |
| Oleic acid | 3 |
| Oleamine with 2 mol of ethylene oxide (Ethomeen O12; Akzo) | 7 |
| Diethylaminopropyl laurylaminosuccinamate, sodium salt, 55% active ingredient | 3.0 AI (*) |
| Oleyl alcohol | 5 |
| Oleic acid diethanolamide | 12 |
| Ethyl alcohol | 7 |
| Propylene glycol | 3.5 |
| Dipropylene glycol | 0.5 |
| Propylene glycol monomethyl ether | 9 |
| Ammonium acetate | 0.8 |
| 20% aqueous ammonia | 10 |
| Demineralized water qs | 100 g |

(*) AI = active ingredient

3. Method

At the time of use, each composition is mixed weight for weight with 20-volume aqueous hydrogen peroxide solution at a pH of 2.3.

The pH of the resulting solutions is 10.1±0.1.

Each mixture is subsequently applied to a lock of natural brown hair (tone level 5).

The leave-on time is 30 minutes at ambient temperature.

At the end of this time, the locks are treated for a minute in an aqueous-alcoholic solution whose composition is given below (amounts expressed in g %):

| Benzyl alcohol | 5 |
|---|---|
| Denatured ethanol | 15 |
| 70 AI hydroxyethyl oleyl dimonium chloride | 5 |
| Benzoic acid | 0.2 |
| Demineralized water | qs 100 |

The locks are then washed with an Elsève Multivitamines® shampoo, rinsed with water and then left to dry.

4. Results

The lightening of the locks is evaluated by colorimetric measurements using a Minolta CM2002 colorimeter.

|  | L* | a* | b* | Lightening (ΔE) |
|---|---|---|---|---|
| Untreated lock | 22.97 | 3.40 | 4.25 | / |
| Inventive composition 1 | 25.83 | 5.94 | 7.85 | 5.25 |
| Inventive composition 2 | 27.51 | 6.12 | 8.59 | 6.85 |
| Prior-art composition | 26.40 | 6.47 | 8.64 | 6.36 |

It is found that the compositions according to the invention enable lightening similar to that of the non-inventive composition, but do not have its disadvantages due to the presence of aqueous ammonia (no significant difference).

EXAMPLE 2

Lightening Composition Containing Direct Dyes

The following invention composition is prepared (the amounts are expressed in g %)

|  | Formula 1 | Formula 2 |
| --- | --- | --- |
| Kaolin | 25 | 25 |
| Sodium carboxymethyl starch | 12 | 12 |
| Isopropyl myristate | 48.25 | 48.25 |
| Fumed silica | 2.25 | 2.25 |
| Sodium lauryl ether sulphate at 70% in water (Texapon AOS 225 UP from Cognis) | 12.5 | 12.5 |
| Disperse Red 17 | 0.99 | — |
| Basic Blue 99 | — | 1.35 |
| (3-Aminopropyl)triethoxysilane | 10 | 10 |

Two formulas are prepared, one based on hydrophilic dye and the other based on hydrophobic dye.

The same procedure is carried out as for the preceding example.

Formula 1 results in a strong dark purplish red.

Formula 2 gives a strong violet.

We claim:

1. A method for coloring and/or lightening human keratin fibers, comprising contacting said fibers with:
   at least one first composition having a water content of less than 10% by weight and comprising at least one aminosilicon compound of formula (I):

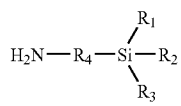

wherein:
$R_1$, $R_2$, and $R_3$, which are identical or different, are chosen from:
linear and branched $C_1$-$C_{20}$ alkoxy radicals wherein the alkyl moiety is optionally interrupted by at least one oxygen atom,
linear and branched $C_2$-$C_{20}$ alkenyloxy radicals,
$R_4$ is a divalent radical of structure:

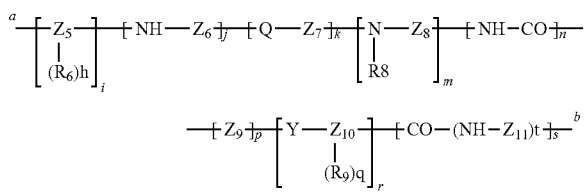

wherein:
$R_6$, identical or different at each occurrence, is chosen from linear and branched $C_1$-$C_4$ alkyl radicals, optionally substituted with at least one hydroxyl group, $NH_2$ radicals, hydroxyl radicals, cyano radicals, a radical $Z_{12}NH_2$, a radical $Z_{13}NH$ $Z_{14}NH_2$, and linear and branched $C_2$-$C_{10}$ alkenyl radicals, with $Z_{12}$, $Z_{13}$, and $Z_{14}$ being chosen from, independently of one another, $C_1$-$C_{20}$ linear alkylene radicals;
$R_8$ is chosen from linear and branched $C_1$-$C_4$ alkyl radicals, optionally substituted with at least one hydroxyl or carboxyl group, linear and branched $C_2$-$C_{10}$ alkenyl radicals, a radical $Z_{15}NH_2$, a radical $Z_{16}R_8'$, and a radical $Z_{17}Si$ $OSi(R_a)_2(R_b)$ wherein:

$R_a$ is chosen from linear and branched $C_1$-$C_4$ alkoxy radicals;
$R_b$ is chosen from linear and branched $C_1$-$C_4$ alkyl radicals;
$Z_{15}$, $Z_{16}$, and $Z_{17}$ are, independently of one another, chosen from $C_1$-$C_{20}$ linear alkylene radicals;
$R_8'$ is chosen from $C_6$-$C_{30}$ aryl radicals;
$R_9$ is chosen from linear and branched $C_1$-$C_4$ alkyl radicals;
$Z_5$, $Z_6$, $Z_7$, $Z_8$, $Z_9$, $Z_{10}$, and $Z_{11}$ are, independently of one another, chosen from $C_1$-$C_{20}$ linear alkylene radicals;
Q is chosen from saturated and unsaturated six-membered rings, optionally comprising at least one heteroatom;
Y, identical or different at each occurrence, is chosen from oxygen, sulfur, and NH groups;
h is an integer chosen from 0, 1, 2, 3, 4, and 5;
i is an integer chosen from 0 and 1;
j is an integer chosen from 0, 1, 2, and 3;
k is an integer chosen from 0 and 1;
m is an integer chosen from 0 and 1;
n is an integer chosen from 0 and 1;
p is an integer chosen from 0 and 1;
q is an integer chosen from 0 and 1;
r is an integer chosen from 0, 1, 2, and 3;
s is an integer chosen from 0 and 1;
wherein at least one of the coefficients h, i, j, k, m, n, p, q, r, and s is non-zero;
a represents the bond to the silicon atom;
b represents the bond to the nitrogen atom of the amino group; and
at least one second composition comprising at least one oxidizing agent.

2. The method according to claim 1, wherein at least one of $R_1$, $R_2$, and $R_3$ is chosen from $C_2$-$C_4$ alkenyloxy radicals.

3. The method according to claim 1, wherein $R_6$, identical or different at each occurrence, is chosen from methyl, ethyl, and linear and branched $C_2$-$C_4$ alkenyl radicals.

4. The method according to claim 1, wherein $R_8$ is chosen from methyl, ethyl, and linear and branched $C_2$-$C_4$ alkenyl radicals.

5. The method according to claim 1, wherein at least one of $Z_{12}$, $Z_{13}$, $Z_{14}$, $Z_{15}$, $Z_{16}$, and $Z_{17}$ is chosen from $C_1$-$C_{10}$ linear alkylene radicals.

6. The method according to claim 1, wherein at least one of $Z_{12}$, $Z_{13}$, $Z_{14}$, $Z_{15}$, $Z_{16}$, and $Z_{17}$ is chosen from $C_1$-$C_4$ linear alkylene radicals.

7. The method according to claim 1, wherein $R_8$ is a phenyl radical.

8. The method according to claim 1, wherein $R_a$ is chosen from methoxy and ethoxy radicals.

9. The method according to claim 1, wherein $R_b$ is chosen from methyl and ethyl radicals.

10. The method according to claim 1, wherein $R_1$ and $R_2$ are identical.

11. The method according to claim 1, wherein the compound of formula (I) comprises only one silicon atom.

12. The method according to claim 1, wherein $R_1$, $R_2$, and $R_3$ are identical.

13. The method according to claim 1, wherein k, n, and s are 0.

14. The method according to claim 1, wherein the at least one aminosilicon compound of formula (I) is present in a total amount ranging from 0.1% to 50% by weight, relative to the weight of the at least one first composition.

15. The method according to claim 1, wherein the at least one first composition comprises at least one coloring agent chosen from: oxidation couplers, oxidation bases, and direct dyes.

16. The method according to claim 1, wherein the at least one first composition comprises at least one fatty substance.

17. The method according to claim 16, wherein the at least one fatty substance is chosen from fatty alcohols, fatty acids, fatty acid esters, fatty alcohol esters, mineral oils, vegetable oils, animal oils, synthetic oils, silicones, and waxes.

18. The method according to claim 17, wherein the at least one fatty substance is chosen from fatty acid esters and liquid petrolatum.

19. The method according to claim 16, wherein the at least one fatty substance is present in a total amount ranging from 10% and 99% by weight, relative to the weight of the at least one first composition.

20. The method according to claim 1, comprising extemporaneously mixing, at the time of use, the at least one first composition and at least one second composition into one composition before contacting the keratin fibers with said composition.

21. The method according to claim 1, comprising contacting the human keratin fibers with the at least one first composition and the at least one second composition successively and without intermediate rinsing.

22. A composition having a water content of less than 10% by weight and comprising at least one aminosilicon compound of formula (I):

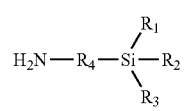

(I)

wherein:
R$_1$, R$_2$, and R$_3$, which are identical or different, are chosen from:
linear and branched C$_1$-C$_{20}$ alkoxy radicals wherein the alkyl moiety is optionally interrupted by at least one oxygen atom,
linear and branched C$_2$-C$_{20}$ alkenyloxy radicals,
R$_4$ is a divalent radical of structure:

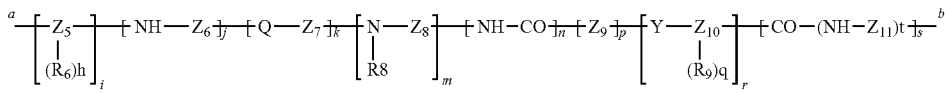

wherein:
R$_6$, identical or different at each occurrence, is chosen from linear and branched C$_1$-C$_4$ alkyl radicals, optionally substituted with at least one hydroxyl group, NH$_2$ radicals, hydroxyl radicals, cyano radicals, a radical Z$_{12}$NH$_2$, a radical Z$_{13}$NH Z$_{14}$NH$_2$, and linear and branched C$_2$-C$_{10}$ alkenyl radicals, with Z$_{12}$, Z$_{13}$, and Z$_{14}$ being chosen from, independently of one another, C$_1$-C$_{20}$ linear alkylene radicals;
R$_8$ is chosen from linear and branched C$_1$-C$_4$ alkyl radicals, optionally substituted with at least one hydroxyl or carboxyl group, linear and branched C$_2$-C$_{10}$ alkenyl radicals, a radical Z$_{15}$NH$_2$, a radical Z$_{16}$R$_8$', and a radical Z$_{17}$Si OSi(R$_a$)$_2$(R$_b$) wherein:
R$_a$ is chosen from linear and branched C$_1$-C$_4$ alkoxy radicals;
R$_b$ is chosen from linear and branched C$_1$-C$_4$ alkyl radicals;
Z$_{15}$, Z$_{16}$, and Z$_{17}$ are, independently of one another, chosen from C$_1$-C$_{20}$ linear alkylene radicals;
R$_8$' is chosen from C$_6$-C$_{30}$ aryl radicals;
R$_9$ is chosen from linear and branched C$_1$-C$_4$ alkyl radicals;
Z$_5$, Z$_6$, Z$_7$, Z$_8$, Z$_9$, Z$_{10}$, and Z$_{11}$ are, independently of one another, chosen from C$_1$-C$_{20}$ linear alkylene radicals;
Q is chosen from saturated and unsaturated six-membered rings, optionally comprising at least one heteroatom;
Y, identical or different at each occurrence, is chosen from oxygen, sulfur, and NH groups;
h is an integer chosen from 0, 1, 2, 3, 4, and 5;
i is an integer chosen from 0 and 1;
j is an integer chosen from 0, 1, 2, and 3;
k is an integer chosen from 0 and 1;
m is an integer chosen from 0 and 1;
n is an integer chosen from 0 and 1;
p is an integer chosen from 0 and 1;
q is an integer chosen from 0 and 1;
r is an integer chosen from 0, 1, 2, and 3;
s is an integer chosen from 0 and 1;
wherein at least one of the coefficients h, i, j, k, m, n, p, q, r, and s is non-zero;
a represents the bond to the silicon atom;
b represents the bond to the nitrogen atom of the amino group; and at least one fatty substance.

23. A multiple-compartment device comprising, in at least one compartment, at least one composition having a water content of less than 10% by weight and comprising at least one aminosilicon compound of formula (I):

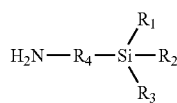

(I)

wherein:
R$_1$, R$_2$, and R$_3$, which are identical or different, are chosen from:
linear and branched C$_1$-C$_{20}$ alkoxy radicals wherein the alkyl moiety is optionally interrupted by at least one oxygen atom,
linear and branched C$_2$-C$_{20}$ alkenyloxy radicals, R$_4$ is a divalent radical of structure:

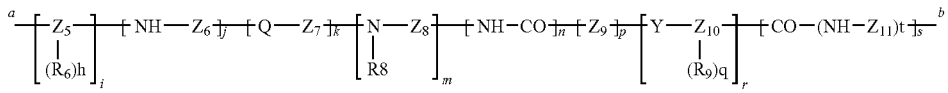

wherein:
- R$_6$, identical or different at each occurrence, is chosen from linear and branched C$_1$-C$_4$ alkyl radicals, optionally substituted with at least one hydroxyl group, NH$_2$ radicals, hydroxyl radicals, cyano radicals, a radical Z$_{12}$NH$_2$, a radical Z$_{13}$NH Z$_{14}$NH$_2$, and linear and branched C$_2$-C$_{10}$ alkenyl radicals, with Z$_{12}$, Z$_{13}$, and Z$_{14}$ being chosen from, independently of one another, C$_1$-C$_{20}$ linear alkylene radicals;
- R$_8$ is chosen from linear and branched C$_1$-C$_4$ alkyl radicals, optionally substituted with at least one hydroxyl or carboxyl group, linear and branched C$_2$-C$_{10}$ alkenyl radicals, a radical Z$_{15}$NH$_2$, a radical Z$_{16}$R$_8$', and a radical Z$_{17}$Si OSi(R$_a$)$_2$(R$_b$) wherein:
- R$_a$ is chosen from linear and branched C$_1$-C$_4$ alkoxy radicals;
- R$_b$ is chosen from linear and branched C$_1$-C$_4$ alkyl radicals;
- Z$_{15}$, Z$_{16}$, and Z$_{17}$ are, independently of one another, chosen from C$_1$-C$_{20}$ linear alkylene radicals;
- R$_8$' is chosen from C$_6$-C$_{30}$ aryl radicals;
- R$_9$ is chosen from linear and branched C$_1$-C$_4$ alkyl radicals;
- Z$_5$, Z$_6$, Z$_7$, Z$_8$, Z$_9$, Z$_{10}$, and Z$_{11}$ are, independently of one another, chosen from C$_1$-C$_{20}$ linear alkylene radicals;
- Q is chosen from saturated and unsaturated six-membered rings, optionally comprising at least one heteroatom;
- Y, identical or different at each occurrence, is chosen from oxygen, sulfur, and NH groups;
- h is an integer chosen from 0, 1, 2, 3, 4, and 5;
- i is an integer chosen from 0 and 1;
- j is an integer chosen from 0, 1, 2, and 3;
- k is an integer chosen from 0 and 1;
- m is an integer chosen from 0 and 1;
- n is an integer chosen from 0 and 1;
- p is an integer chosen from 0 and 1;
- q is an integer chosen from 0 and 1;
- r is an integer chosen from 0, 1, 2, and 3;
- s is an integer chosen from 0 and 1;
- wherein at least one of the coefficients h, i, j, k, m, n, p, q, r, and s is non-zero;
- a represents the bond to the silicon atom;
- b represents the bond to the nitrogen atom of the amino group;

and at least one fatty substance;
and in at least one other compartment, at least one composition comprising at least one oxidizing agent.

* * * * *